(12) United States Patent
Niehrs et al.

(10) Patent No.: US 10,538,563 B2
(45) Date of Patent: Jan. 21, 2020

(54) RSPONDINS AS MODULATORS OF ANGIOGENESIS AND VASCULOGENESIS

(71) Applicant: DEUTSCHES KREBSFORSCHUNGSZENTRUM STIFTUNG DES ÖFFENTLICHEN RECHTS, Heidelberg (DE)

(72) Inventors: Christof Niehrs, Mainz (DE); Olga Kazanskaya, Buchen (DE); Bisei Okawara, Yokkaichi (JP)

(73) Assignee: DEUTSCHES KREBSFORSCHUNGSZENTRUM STIFTUNG DES OFFENTLICHEN RECHTS, Heidelberg (DE)

( * ) Notice: Subject to any disclaimer, the term of this patent is extended or adjusted under 35 U.S.C. 154(b) by 0 days.

(21) Appl. No.: 16/357,765

(22) Filed: Mar. 19, 2019

(65) Prior Publication Data

US 2019/0359664 A1 Nov. 28, 2019

Related U.S. Application Data

(60) Continuation of application No. 14/870,846, filed on Sep. 30, 2015, now Pat. No. 10,273,276, which is a continuation of application No. 14/453,692, filed on Aug. 7, 2014, now Pat. No. 9,226,963, which is a division of application No. 14/048,225, filed on Oct. 8, 2013, now Pat. No. 8,926,970, which is a continuation of application No. 13/309,193, filed on Dec. 1, 2011, now Pat. No. 8,580,736, which is a division of application No. 12/311,921, filed as application No. PCT/EP2007/009105 on Oct. 19, 2007, now Pat. No. 8,088,374.

(30) Foreign Application Priority Data

Oct. 20, 2006 (EP) .................................... 06022070

(51) Int. Cl.

| A61K 48/00 | (2006.01) |
|---|---|
| C07H 21/02 | (2006.01) |
| C07H 21/04 | (2006.01) |
| C07K 14/475 | (2006.01) |
| C12Q 1/6883 | (2018.01) |
| C07K 16/18 | (2006.01) |
| A61K 38/17 | (2006.01) |
| C12N 15/113 | (2010.01) |
| G01N 33/74 | (2006.01) |
| C07K 14/515 | (2006.01) |
| A61K 39/395 | (2006.01) |

(52) U.S. Cl.
CPC ........ C07K 14/475 (2013.01); A61K 38/1703 (2013.01); A61K 39/3955 (2013.01); C07K 14/515 (2013.01); C07K 16/18 (2013.01); C12N 15/1136 (2013.01); C12Q 1/6883 (2013.01); G01N 33/74 (2013.01); C07K 2317/76 (2013.01); C12N 2310/111 (2013.01); C12N 2310/14 (2013.01); C12N 2310/3233 (2013.01); C12Q 2600/106 (2013.01); G01N 2800/52 (2013.01); Y10T 436/143333 (2015.01)

(58) Field of Classification Search
CPC ............................ C12N 15/113; A61K 31/713
See application file for complete search history.

(56) References Cited

U.S. PATENT DOCUMENTS

| 6,485,972 B1 | 11/2002 | McMahon et al. |
|---|---|---|
| 6,653,448 B1 | 11/2003 | Vernet et al. |
| 6,824,973 B2 | 11/2004 | Tang et al. |
| 7,319,141 B2 | 1/2008 | Tang et al. |
| 7,320,880 B2 | 1/2008 | Nishikawa et al. |
| 7,411,052 B2 | 8/2008 | Tang |
| 7,439,327 B2 | 10/2008 | Boyle et al. |
| 7,439,332 B2 | 10/2008 | Nishikawa et al. |
| 7,541,431 B2 | 6/2009 | Yoon |
| 7,674,890 B2 | 3/2010 | Boyle et al. |
| 8,158,757 B2 | 4/2012 | Gurney et al. |
| 8,158,758 B2 | 4/2012 | Gurney |
| 2001/0055790 A1 | 12/2001 | Barnes et al. |

(Continued)

FOREIGN PATENT DOCUMENTS

| EP | 2157192 | 8/2013 |
|---|---|---|
| WO | WO98041539 | 9/1998 |

(Continued)

OTHER PUBLICATIONS

Chen, et al., 2002, Mol. Biol. rep. 29, 287-292.

(Continued)

*Primary Examiner* — Amy H Bowman
(74) *Attorney, Agent, or Firm* — Hoffmann & Baron, LLP

(57) ABSTRACT

The present invention relates to the use of Rspondins, particularly Rspondin2 (Rspo2) or Rspondin3 (Rspo3) or Rspondin nucleic acids, or regulators or effectors or modulators of Rspondin, e.g. Rspo2 and/or Rspo3 to promote or inhibit angiogenesis and/or vasculogenesis, respectively. The invention is based on the demonstration that Rspo3 and Rspo2 are angiogenesis promoters, and the identification of Rspo2 and 3 as positive regulators of vascular endothelial growth factor (VEGF). These results indicate a major role for Rspondins, particularly Rspo3 and/or Rspo2 in the signaling system during angiogenesis. The invention also relates to the use of regulators or effectors or modulators of Rspondin3, including agonists and antagonists, in the treatment of conditions where treatment involves inhibiting or promoting angiogenesis and/or vasculogenesis.

3 Claims, 11 Drawing Sheets

Figure 1:
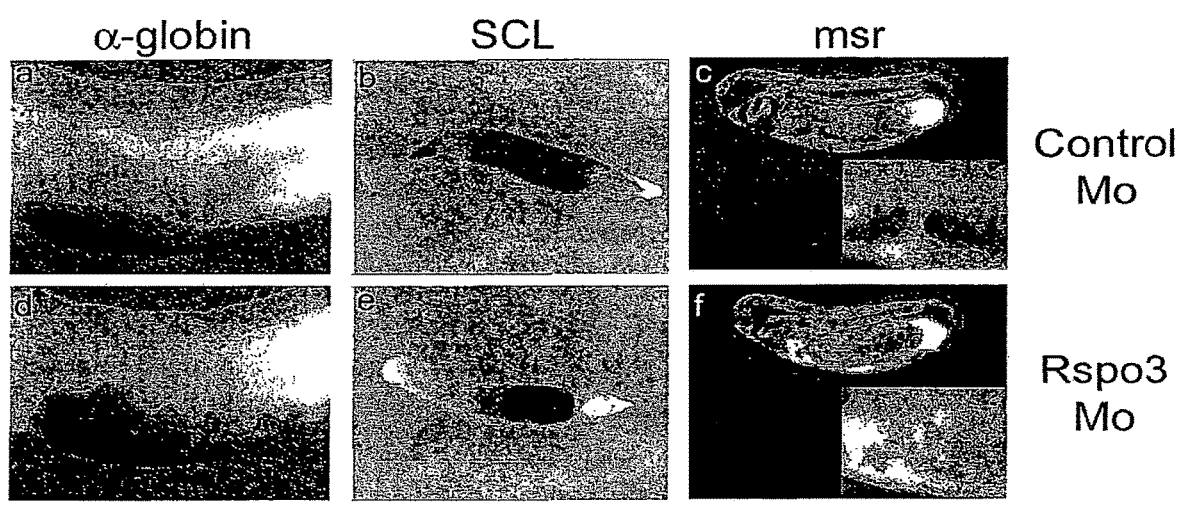

Specification includes a Sequence Listing.

(56) References Cited

U.S. PATENT DOCUMENTS

| | | | |
|---|---|---|---|
| 2002/0065394 | A1 | 5/2002 | Jacobs et al. |
| 2003/0017480 | A1 | 1/2003 | Ota et al. |
| 2003/0022217 | A1 | 1/2003 | Ceccardi et al. |
| 2003/0022255 | A1 | 1/2003 | Morris et al. |
| 2003/0044792 | A1 | 3/2003 | Tang et al. |
| 2003/0198975 | A1 | 10/2003 | Azimzai et al. |
| 2004/0077048 | A1 | 4/2004 | Warren et al. |
| 2005/0054829 | A1 | 3/2005 | Wiley et al. |
| 2005/0059073 | A1 | 3/2005 | Tang et al. |
| 2006/0149049 | A1 | 7/2006 | Tang |
| 2007/0244061 | A1 | 10/2007 | Niehrs et al. |
| 2009/0036369 | A1 | 2/2009 | Kakitani et al. |
| 2009/0118176 | A1 | 5/2009 | Emtage et al. |
| 2010/0278800 | A1 | 11/2010 | Boyle et al. |
| 2011/0091454 | A1 | 4/2011 | Diber et al. |
| 2013/0095116 | A1 | 4/2013 | Gurney et al. |
| 2013/0115206 | A1 | 5/2013 | Gurney et al. |
| 2013/0121993 | A1 | 5/2013 | Gurney |

FOREIGN PATENT DOCUMENTS

| | | |
|---|---|---|
| WO | WO98049302 | 11/1998 |
| WO | 20010007611 | 2/2001 |
| WO | 20010077169 | 10/2001 |
| WO | WO01077169 | 10/2001 |
| WO | WO02060942 | 8/2002 |
| WO | WO03004676 | 1/2003 |
| WO | WO03025142 | 3/2003 |
| WO | WO03027230 | 4/2003 |
| WO | WO03029405 | 4/2003 |
| WO | WO03094843 | 11/2003 |
| WO | WO04080148 | 9/2004 |
| WO | WO04099408 | 11/2004 |
| WO | 2005040418 | 5/2005 |
| WO | WO05040418 | 5/2005 |

OTHER PUBLICATIONS

Kamata, et al., 2004, Biochim,. Biophys. Acta., 1676, 51-62.
Kazanskaya, et al., 2004, Dev. Cell, 7, 525-534.
Kim, et al., 2005, Science 309, 1256-1259.
Kim, et al., 2006, Cell Cycle 5, 23-26.
Nam, et al., 2006, J. Biol. Chem. 281, 13247-13257.
Aoki, et al., Dev. Biol. 2007, 301(1):218-26.
Ferrara, 2005, Oncology 3:11-6.
Rosen, 2005, Oncologist 10:382-91.
Mead, et al., 1998, Development 125, 2611-2620.
Devic, et al., 1996, Mech Dev. 1996; 59, 129-140.
Goodwin, et al., "Wnt signaling in the vasculature," 2002, Angiogenesis, 5:1-9.
Bienz, M et al (2000) Linking colorectal cancer to Wnt signaling Cell 103(2):311-320.
Brantjes, H et al (2002) TCF: Lady Justice casting the final verdict on the outcome of Wnt signaling Bio Chem 383(2):255-261.
Chen, JZ et al (2002) Cloning and identification of a cDNA that encodes a novel human protein with thrombospondin type I repeat domain, hPWTSR Mol Biol Rep 29(3):287-292.
Easwaran, V et al (2003) beta-Catenin regulates vascular endothelial growth factor expression in colon cancer Cancer Res. 63(12):3145-3153.
European Search Report for EP21575192, dated Dec. 22, 2009.
GenBank AF251057.1 extract (2000) Homo sapiens clone 1 thrombospondin mRNA, complete cds; cited D1a in Opposition filed Jun. 11, 2014 for EP Application 09170230.8.
Giles, RH et al (2003) Caught up in a Wnt storm: Wnt signaling in cancer Biochim Biophys Acta 1653(1):1-24.
Goldblum, SE et al (1999) Thrombospondin-1 induces tyrosine phosphorylation of adherens junction proteins and regulates an endothelial paracellular pathway Mol Biol Cell 10(5):1537-1551.
Hartman, C (2002) Wnt-signaling and skeletogenesis J Musculoskelet Neuronal Interact 2(3):274-276.
Horesh, Y et al (2003) A rapid method for detection of putative RNAi target genes in genomic data Bioinformatics 19(Suppl. 2):ii73-80.
Horesh, Y et al Publication information D14a in Opposition EP filed Jun. 11, 2014 in EP Application #09170230.8.
International Preliminary Report on Patentability (Chapter I) for PCT/EP2004/011269.
International Search Report for WO05/040418, dated Aug. 23, 2005 (PCT/EP2004/011269).
Jackson, AL et al (2004) Noise amidst the silence: off-target effects of siRNAs? Trends Genet 20(11):521-524.
Kamata, T et al (2004) R-spondin, a novel gene with thrombospondin type 1 domain, was expressed in the dorsal neural tube and affected in Wnts mutants Biochim Biophys ACTA 1676(1):51-62.
Kazanskay, O et al (2004) R-Spondin2 is a secreted activator of Wnt/beta-catenin signaling and is required for Xenopus myogenesis Dev Cell 7(4):525-534.
Kim, KA et al (2005) Mitogenic influence of human R-spondin1 on the intestinal epithelium Science 309(5738):1256-1259.
Kim, KA et al (2006) R-Spondin proteins: a novel link to beta-catenin activation Cell Cycle 5(1):23-26.
Lonberg, N (2005) Human antibodies from transgenic animals Nat Biotechnol 23(9):1117-1125.
Meniel, V et al (2003) Wnt-cadherin connections in normal and neoplastic mammary epithelium J Mammary Gland Biol Neoplasia 8(4):435-447.
Nam, JS et al (2006) Mouse cristin/R-spondin family proteins are novel ligands for the Frizzled 8 and LRP6 receptors and activate beta-catenin-dependent gene expression J. Biol Chem 281(19):13247-13257.
Office Action for U.S. Appl. No. 10/575,217 (US2007/0244061) dated May 4, 2011.
Opposition filed for EP2157192 (EP App. No. 091702308) filed Jun. 11, 2014.
Peifer, M et al (2000) Wnt signaling in oncogenesis and embryogenesis—a look outside the nucleus Science 287(5458):1606-1609.
Perantoni, AO (2003) Renal development: perspectives on a Wnt-dependent process Semin Cell Dev Biol.14(4):201-208.
Polakis, P (2000) Wnt signaling and cancer Genes Dev.14(15):1837-1851.
Polesskaya, A et al (2003) Wnt signaling induces the myogenic specification of resident CD45+ adult stem cells during muscle regeneration Cell 113(7):841-52.
Prockop, DJ et al (2003) One strategy for cell and gene therapy: harnessing the power of adult stem cells to repair tissues Proc Natl Acad Sci U S A. 100(Suppl.1):11917-11923.
SEQ ID No. 9 from WO01/077169,encodes SEQ ID No. 10.
SEQ ID No. 33 from WO01/077169, encodes SEQ ID No. 34.
Stump, RJW et al (2003) A role for Wnt/beta-catenin signaling in lens epithelial differentiation Dev Biol 259(1):48-61.
Van Es, JH et al (2003) You Wnt some, you lose some: oncogenes in the Wnt signaling pathway Curr Opin Genet Dev 13(1):28-33.
Wu, W et al (2000) Mutual antagonism between dickkopf1 and dickkopf2 regulates Wnt/beta-catenin signaling Curr Biol 10(24):1611-1614.

SEQUENCE LISTING

<160> NUMBER OF SEQ ID NOS: 23

<210> SEQ ID NO 1
<211> LENGTH: 1432
<212> TYPE: DNA
<213> ORGANISM: Xenopus laevis

<400> SEQUENCE: 1

```
gggggtgatt tcaaggccgt ccaaatgcag tttcaactct tttcattcgc cctgatcatc      60
ctgaactgtg tggattacag tcactgccaa gcctcccgct ggagacggag caagagagcc     120
agctatggga ccaacccgat atgcaaaggt tgcctgtcct gctcaaaaga taatgggtgc     180
ctccgctgcc agccaaaact gttttctttt ctgcgaagag aaggtatgag gcagtatgga     240
gagtgtctgc agtcctgccc tccgggatac tatggagtca gaggacctga tatgaacagg     300
tgttccagat gcagaattga aaattgcgac tcttgtttta gtagagattt ttgcataaag     360
tgcaaatcgg gcttttactc cctcaagggg caatgctttg aagaatgccc agaaggattt     420
gcaccactgg atgataccat ggtgtgtgtg gatggctgcg aagtagggcc atggagtgaa     480
tggggcacat gcagccgaaa taacagaacg tgcggtttca aatgggcct ggagaccaga     540
acgcgacaaa ttgtgaagaa accagcaaaa gacaccatcc cctgcccaac tattgctgaa     600
tccagaagat gtaagatggc aataagacac tgccctggag gaaagagaac tacaaagaag     660
aaggacaaga ggaacaagaa gaagaaaaag aagttactgg agagggccca agagcagcac     720
agcgtcgtcc ttgctacaga ccggtctagc caatagagac agatccttac attttctttt     780
tttgctaagt gcacaacggc tgctacatgc tcttgcacac gaatgaactg cggaaccgct     840
gctttaacag tattggttgc aaataacatg tgaaccgatt cacaaggttg tttgtgttat     900
ttatacattt ttaattttt tttcctcaat ccggaacttc caaaaaggag tgaacgctga     960
gttgaatcag tgttgtagtt gggacaaagg attttttttt taattattgt ttcttcggtt    1020
tttattgtag tgcctgtgag gggcactggc agaattcttt ttggaaaagg aactgttgta    1080
gaaattgcag aagctatcta caactactcg gacttgtgta tatttctgtg aaaggaaaaa    1140
aaaacagaat aaagaaaccc cttggtggga ccgacccaat atcatttttt tttgcttgtt    1200
ttacatactg tacatttcac gattgtacat gaaatatttg tttaggtgat gtttgttccc    1260
agcgcctatt ttattaaaac agttgtataa tgaaactgtt taagctaata tactgtacta    1320
cagaggtaac tgcttattgt cccttgtagc ctattggtta tttgtacata gtgctgagaa    1380
gctacacata ataaacttat ttactgtgta aaaaaaaaa aaaaaaaaaa aa             1432
```

<210> SEQ ID NO 2
<211> LENGTH: 786

<212> TYPE: DNA
<213> ORGANISM: Xenopus tropicalis

<400> SEQUENCE: 2

```
cattacaagg ttactatgca attgcgactg cttctctgt gttttatcat attgaacttc     60
ttggaataca ttgacagcca gcagatcccc agagggaggc gacatcggag aatgcatcct   120
aatgtcagcc agggttgcca aggaggatgt gctacatgtt ctgattataa tggctgttta   180
acatgcaagc ctcagctgtt tttcgctttg gtaagaaatg gaatgaagca aattggagtc   240
tgtcgtccct cctgtccaaa tggatatttt gggatacgat caccagaaat aaataaatgt   300
acaaaatgca aagctgactg tgaaacatgt ttcaacaaaa atttctgcac aaagtgtaaa   360
agtggatttt acaaacacaa cggaaagtgc ttagacacat gtcctgaagg gtttgagaac   420
aatcacaata tggagtgcac cagtgtggtg cactgcgtag ttggggagtg gagcgcttgg   480
ggtccgtgca caaagagggg gaaaacctgt gacatcaagc gaggaaatga acaagggtt    540
cgggaaattt tacaataccc ttcacctagg ggcacaccct gtccgccaac atccgagaca   600
aaaaaatgtg tagtaaagag aaagaaatgt caagacagtc aagacagaca aaggccaaga   660
ggcaacagag atgaaataaa aaagaataaa caaaggcgaa agaatggtga cgctcccaga   720
aaacaaagac agagaaagca agagagaaat cagcgagaag gaaagagagg ggagggcaaa   780
gtctaa                                                               786
```

<210> SEQ ID NO 3
<211> LENGTH: 946
<212> TYPE: DNA
<213> ORGANISM: Mus musculus

<400> SEQUENCE: 3

```
tcctgctcag aacgccagaa gcagctcggg tctctccagc gcccccttgac catggctgcg    60
gtacccacgg cgtccgcttc cctgcgctcc cggggtccct gccacagccg cagccgctgc   120
agcctctgag ccccaggggc cactgctcgc ctggattccg cccgcagccg ccgctgctgt   180
gcaaccgagg ctaacctgcg gccagccagg aggctcctgc aaccttcgct cgcggcgatg   240
acagccaccc cagagcagcc ggctgtgttc ggacaatttg agaatgcaat tgttggtttc   300
ccggtccacc cgtcccgctt cgcttgccat cacagcacgc ctgttggatc tcagtggaga   360
agtcccgctg ctctggtttt tctactcttc gtatagactc gcctaacacc tacatacata   420
ttttctctta aaaaaaaaca ttaaatataa ctaacagtga aagaaaaag gagagaaaaa    480
agggaaacat tacagggtta ctatgcactt gcgactgatt tcttgttttt ttatcatttt   540
gaactttatg gaatacattg gcagccaaaa cgcctcccga ggaaggcgcc agcgaagaat   600
gcatcctaat gtcagtcaag gctgccaagg aggctgtgca acgtgttcag attacaatgg   660
ctgtttgtca tgtaagccca gactgttttt tgttctggaa aggattggca tgaagcagat   720
aggagtgtgt ctctcttcgt gtccaagtgg atattacgga actcgatatc cagatataaa   780
taaatgtaca aaatgcaaag ttgactgtga tacctgtttc aacaaaatt tctgcacaaa     840
gtgtaaaagt ggattttact tacaccttgg aaagtgcctt gacagttgcc cagaagggtt   900
agaagccaac aatcatacta tggaatgtgt cagtattgat cagtaa                 946
```

<210> SEQ ID NO 4
<211> LENGTH: 20
<212> TYPE: DNA
<213> ORGANISM: Artificial Sequence
<220> FEATURE:

```
<223> OTHER INFORMATION: primer pair F1

<400> SEQUENCE: 4
atgctttgag gcttgtgacc                                               20

<210> SEQ ID NO 5
<211> LENGTH: 20
<212> TYPE: DNA
<213> ORGANISM: Artificial sequence
<220> FEATURE:
<223> OTHER INFORMATION: primer pair R1

<400> SEQUENCE: 5
tgcaccgact ccagtactgg                                               20

<210> SEQ ID NO 6
<211> LENGTH: 22
<212> TYPE: DNA
<213> ORGANISM: Artificial sequence
<220> FEATURE:
<223> OTHER INFORMATION: primer Trio 3rd

<400> SEQUENCE: 6
tacattctgg tttctcatct gg                                            22

<210> SEQ ID NO 7
<211> LENGTH: 20
<212> TYPE: DNA
<213> ORGANISM: Artificial sequence
<220> FEATURE:
<223> OTHER INFORMATION: XSCL forward

<400> SEQUENCE: 7
actcaccctc cagacaagaa                                               20

<210> SEQ ID NO 8
<211> LENGTH: 20
<212> TYPE: DNA
<213> ORGANISM: Artificial sequence
<220> FEATURE:
<223> OTHER INFORMATION: XSCL reverse

<400> SEQUENCE: 8
atttaatcac cgctgcccac                                               20

<210> SEQ ID NO 9
<211> LENGTH: 20
<212> TYPE: DNA
<213> ORGANISM: Artificial sequence
<220> FEATURE:
<223> OTHER INFORMATION: A-globin forward

<400> SEQUENCE: 9
tccctcagac caaaacctac                                               20

<210> SEQ ID NO 10
<211> LENGTH: 21
<212> TYPE: DNA
<213> ORGANISM: Artificial sequence
<220> FEATURE:
<223> OTHER INFORMATION: A-globin reverse

<400> SEQUENCE: 10
cccctcaatt ttatgctgga c                                             21
```

```
<210> SEQ ID NO 11
<211> LENGTH: 24
<212> TYPE: DNA
<213> ORGANISM: Artificial sequence
<220> FEATURE:
<223> OTHER INFORMATION: Xmsr forward primer

<400> SEQUENCE: 11
aacttcgctc tcgctcctcc atac                                             24

<210> SEQ ID NO 12
<211> LENGTH: 22
<212> TYPE: DNA
<213> ORGANISM: Artificial sequence
<220> FEATURE:
<223> OTHER INFORMATION: Xmsr reverse primer

<400> SEQUENCE: 12
gccagcagat agcaaacacc ac                                               22

<210> SEQ ID NO 13
<211> LENGTH: 20
<212> TYPE: DNA
<213> ORGANISM: Artificial sequence
<220> FEATURE:
<223> OTHER INFORMATION: VEGF forward primer

<400> SEQUENCE: 13
aggcgaggga gaccataaac                                                  20

<210> SEQ ID NO 14
<211> LENGTH: 20
<212> TYPE: DNA
<213> ORGANISM: Artificial sequence
<220> FEATURE:
<223> OTHER INFORMATION: VEGF reverse primer

<400> SEQUENCE: 14
tctgctgcat tcacactgac                                                  20

<210> SEQ ID NO 15
<211> LENGTH: 25
<212> TYPE: DNA
<213> ORGANISM: Artificial sequence
<220> FEATURE:
<223> OTHER INFORMATION: antisense morpholino oliogonucleotide

<400> SEQUENCE: 15
atgcaattgc gactgctttc tctgt                                            25

<210> SEQ ID NO 16
<211> LENGTH: 2995
<212> TYPE: DNA
<213> ORGANISM: Homo sapiens

<400> SEQUENCE: 16
gcgaccggcc agagtagggc atccgctcgg gtgctgcgga gaacgagggc agctccgagc      60
cgccccggag gaccgatgcg ccgggtgggg cgctggcccc gagggcgtga gccgtccgca     120
gattgagcaa cttgggaacg ggcggcgga gcgcaggcga gccgggcgcc caggacagtc      180
ccgcagcggg cgggtgagcg ggccgcgccc tcgcccctcc cgggcctgcc cccgtcgcga     240
ctggcagcac gaagctgaga ttgtggtttc ctggtgattc aggtgggagt gggccagaag     300
atcaccgctg gcaaggactg gtgtttgtca actgtaagga ctcatggaac agatctacca    360
```

```
gggattctca gaccttagtt tgagaaatgc tgcaattaaa ggcaaatcct atcactctga    420
gtgatcgctt tggtgtcgag gcaatcaacc ataaagataa atgcaaatat ggaaattgca    480
taacagtact cagtattaag gttggttttt ggagtagtcc ctgctgacgt gacaaaaaga    540
tctctcatat gatattccga ggtatctttg aggaagtctc tctttgagga cctcccttg     600 agctgatgga gaactgggct ccccacaccc tctctgtccc cagctgagat tatggtggat    660
ttgggctacg gcccaggcct gggcctcctg ctgctgaccc agcccagag gtgttagcaa     720 gagccgtgtg ctatccaccc tccccgagac caccctccg accaggggcc tggagctggc     780
gcgtgactat gcggcttggg ctgtgtgtgg tggccctggt tctgagctgg acgcacctca    840
ccatcagcag ccggggatc aaggggaaaa ggcagaggcg gatcagtgcc gaggggagcc     900
aggcctgtgc caaaggctgt gagctctgct ctgaagtcaa cggctgcctc aagtgctcac    960
ccaagctgtt catcctgctg gagaggaacg acatccgcca ggtgggcgtc tgcttgccgt   1020
cctgcccacc tggatacttc gacgcccgca accccgacat gaacaagtgc atcaaatgca   1080
agatcgagca ctgtgaggcc tgcttcagcc ataacttctg caccaagtgt aaggagggct   1140
tgtacctgca aagggccgc tgctatccag cttgtcccga gggctcctca gctgccaatg    1200
gcaccatgga gtgcagtagt cctgcgcaat gtgaaatgag cgagtggtct ccgtgggggc   1260
cctgctccaa gaagcagcag ctctgtggtt tccggagggg ctccgaggag cggacacgca   1320
gggtgctaca tgcccctgtg ggggaccatg ctgcctgctc tgacaccaag gagacccgga   1380
ggtgcacagt gaggagagtg ccgtgtcctg aggggcagaa gaggaggaag ggaggccagg   1440
gccggcggga gaatgccaac aggaacctgg ccaggaagga gagcaaggag gcgggtgctg   1500
gctctcgaag acgcaagggg cagcaacagc agcagcagca agggacagtg gggccactca   1560
catctgcagg gcctgcctag ggacactgtc cagcctccag gcccatgcag aaagagttca   1620
gtgctactct gcgtgattca agctttcctg aactggaacg tcggggcaa agcatacaca    1680 cacactccaa tccatccatg catacataga cacaagacac acgctcaa acccctgtcc      1740 acatatacaa ccatacatac ttgcacatgt gtgttcatgt acacacgcag acacagacac   1800
cacacacaca catacacaca cacacacaca cacacctgag gccaccagaa gacacttcca   1860
tccctcgggc ccagcagtac acacttggtt tccagagctc ccagtggaca tgtcagagac   1920
aacacttccc agcatctgag accaaactgc agagggagc cttctggaga agctgctggg    1980
atcggaccag ccactgtggc agatgggagc caagcttgag gactgctggt gacctgggaa   2040
gaaaccttct tcccatcctg ttcagcactc ccagctgtgt gactttatcg ttggagagta   2100
ttgttaccct tccaggatac atatcagggt taacctgact ttgaaaactg cttaaaggtt   2160
tatttcaaat taaacaaaa aaatcaacga cagcagtaga cacaggcacc acattccttt    2220
gcagggtgtg agggtttggc gaggtatgcg taggagcaag aagggacagg gaatttcaag   2280
agacccaaaa tagcctgctc agtagagggt catgcagaca aggaagaaaa cttaggggct   2340
gctctgacgg tggtaaacag gctgtctata tccttgttac tcagagcatg gcccggcagc   2400
agtgttgtca cagggcagct tgttaggaat gagaatctca ggtctcattc cagacctggt   2460
gagccagagt ctaaatttta agattcctga tgattggcat gttacccaaa tttgagaagt   2520
gctgctgtaa ttcccttaa aggacgggag aaagggcccc ggccatcttg cagcaggagg    2580
gattctggtc agctataaag gaggactttc catctgggag aggcagaatc tatatactga   2640
agggctagtg gcactgccag gggaagggag tgcgtaggct tccagtgatg gttgggaca    2700 atcctgccca aaggcagggc agtggatgga ataactcctt gtggcattct gaagtgtgtg   2760
```
ccaggctctg gactaggtgc taggtttcca gggaggagcc aaacacgggc cttgctcttg    2820
tggagcttag aggttggtgg ggaagaaaat aggcatgcac caaggaattg tacaaacaca    2880
tatataacta caaaaggatg gtgccaaggg caggtgacca ctggcatcta tgcttagcta    2940
tgaaagtgaa taaagcagaa taaaaataaa atactttctc tcaggaaaaa aaaaa         2995

<210> SEQ ID NO 17
<211> LENGTH: 263
<212> TYPE: PRT
<213> ORGANISM: Homo sapiens

<400> SEQUENCE: 17

Met Arg Leu Gly Leu Cys Val Val Ala Leu Val Leu Ser Trp Thr His
1               5                   10                  15

Leu Thr Ile Ser Ser Arg Gly Ile Lys Gly Lys Arg Gln Arg Arg Ile
            20                  25                  30

Ser Ala Glu Gly Ser Gln Ala Cys Ala Lys Gly Cys Glu Leu Cys Ser
        35                  40                  45

Glu Val Asn Gly Cys Leu Lys Cys Ser Pro Lys Leu Phe Ile Leu Leu
    50                  55                  60

Glu Arg Asn Asp Ile Arg Gln Val Gly Val Cys Leu Pro Ser Cys Pro
65                  70                  75                  80

Pro Gly Tyr Phe Asp Ala Arg Asn Pro Asp Met Asn Lys Cys Ile Lys
                85                  90                  95

Cys Lys Ile Glu His Cys Glu Ala Cys Phe Ser His Asn Phe Cys Thr
            100                 105                 110

Lys Cys Lys Glu Gly Leu Tyr Leu His Lys Gly Arg Cys Tyr Pro Ala
        115                 120                 125

Cys Pro Glu Gly Ser Ser Ala Ala Asn Gly Thr Met Glu Cys Ser Ser
    130                 135                 140

Pro Ala Gln Cys Glu Met Ser Glu Trp Ser Pro Trp Gly Pro Cys Ser
145                 150                 155                 160

Lys Lys Gln Gln Leu Cys Gly Phe Arg Arg Gly Ser Glu Glu Arg Thr
                165                 170                 175

Arg Arg Val Leu His Ala Pro Val Gly Asp His Ala Ala Cys Ser Asp
            180                 185                 190

Thr Lys Glu Thr Arg Arg Cys Thr Val Arg Arg Val Pro Cys Pro Glu
        195                 200                 205

Gly Gln Lys Arg Arg Lys Gly Gly Gln Gly Arg Arg Glu Asn Ala Asn
    210                 215                 220

Arg Asn Leu Ala Arg Lys Glu Ser Lys Glu Ala Gly Ala Gly Ser Arg
225                 230                 235                 240

Arg Arg Lys Gly Gln Gln Gln Gln Gln Gln Gly Thr Val Gly Pro
                245                 250                 255

Leu Thr Ser Ala Gly Pro Ala
            260

<210> SEQ ID NO 18
<211> LENGTH: 2842
<212> TYPE: DNA
<213> ORGANISM: Homo sapiens

<400> SEQUENCE: 18
tggaattcca gagctgccag gcgctcccag ccggtctcgg caaacttttc cccagcccac      60
gtgctaacca agcggctctc ttcccgagcc cgggatggag caccgcgcct agggaggccg     120

```
cgccgcccga gacgtgcgca cggttcgtgg cggagagatg ctgatcgcgc tgaactgacc    180
ggtgcggccc gggggtgagt ggcgagtctc cctctgagtc ctccccagca gcgcggccgg    240
cgccggctct ttgggcgaac cctccagttc ctagactttg agaggcgtct ctcccccgcc    300
cgaccgccca gatgcagttt cgccttttct cctttgccct catcattctg aactgcatgg    360
attacagcca ctgccaaggc aaccgatgga gacgcagtaa gcgagctagt tatgtatcaa    420
atcccatttg caagggttgt ttgtcttgtt caaaggacaa tgggtgtagc cgatgtcaac    480
agaagttgtt cttcttcctt cgaagagaag ggatgcgcca gtatggagag tgcctgcatt    540
cctgcccatc cgggtactat ggacaccgag ccccagatat gaacagatgt gcaagatgca    600
gaatagaaaa ctgtgattct tgctttagca aagacttttg taccaagtgc aaagtaggct    660
tttatttgca tagaggccgt tgctttgatg aatgtccaga tggttttgca ccattagaag    720
aaaccatgga atgtgtggaa ggatgtgaag ttggtcattg gagcgaatgg ggaacttgta    780
gcagaaataa tcgcacatgt ggatttaaat ggggtctgga aaccagaaca cggcaaattg    840
ttaaaaagcc agtgaaagac acaataccgt gtccaaccat tgctgaatcc aggagatgca    900
agatgacaat gaggcattgt ccaggaggga agagaacacc aaaggcgaag gagaagagga    960
acaagaaaaa gaaaaggaag ctgatagaaa gggcccagga gcaacacagc gtcttcctag   1020
ctacagacag agctaaccaa taaaacaaga gatccggtag atttttaggg gttttttgttt   1080 ttgcaaatgt gcacaaagct actctccact cctgcacact ggtgtgcagc ctttgtgctg   1140
ctctgcccag tatctgttcc cagtaacatg gtgaaaggaa gcaccaccag catggcccct   1200
gtgttattta tgctttgatt tgaatctgga gactgtgaag gcaggagtaa gtgcacagcc   1260
cgtgacttgg ctcagtgtgt gctgagagaa tccgtccccg gcaccatgga catgctagag   1320
gtgtgaggct gcagaacacc gctggaggac ggacttgtgc ctatttatgt gaaagaagat   1380
gcttggcagg caatgcgcta ctcactcgtg acctttattt ctcacattgt gcattttcaa   1440
ggatatgttt gtgtggatat ctgcttagtg ttaccacatg gtattctcag catgttacct   1500
tcacactgtt gtgcgatgaa actgctttta gctgaggata tgctctggaa attcctgctc   1560
agtttcactg cagccctaat atgtacatat actgcaggag ctacatataa agctcttatt   1620
tactgtatat ttatgctttc ttgtgggtaa caagtcatac ctgattaata tgatgccact   1680
ttgtttctag tggttcctaa cccattgtct gataaatgac ttttctagtt tggggaattg   1740
acacttgttt tgttgcctct tgaaactttt ttttttttccc ctcattgtgg gcttatttct   1800
cattgtaagg gtaggataaa ctagtttttg tatatagagt caaatgacca gtgtcaaaga   1860
gtttgcatat tgggtagacc ttctccactc cacatgtccc acacatatag ataaagcagc   1920
aggcggcatc tggcaatcag aagcccaaac tgcctttgag tctaagatgt gatgactttg   1980
atgaaacaca actgaaaaca tgagggacta tatccagtca cttgtagcca gtttcacagg   2040
ccagctacag aattgtccaa acaaacatta tttctgactg caattttttt cccccaaatt   2100
taaagcaatc cctggcttta aatgacaagg cacctaccaa tgttcttggg tcactgaaga   2160
agctactacc atgagcctgt gcatagaatt ttaggagata aaaggatgaa tttctgtgac   2220
tgccagtcag atcttaacag gtttctgttg agccagaatc tgtttcagat ccaagatgga   2280
gaggaacact atggaaactt cccaggtgac tttcagagca gttgtttcaa acacatcatt   2340
gtccttttag gggaaccagt ttttagaagg ttgtgaattg ctttttttcac aaagcatgat   2400 tatcttcctg gctgatccag gagaaaatta gaacagaaaa ataatggttg tggattttga   2460
```

```
aacaaagcaa ggtaaagcct ttttttttc accttgcatt ggcaaaacta cctcttcagt       2520
gtttttaact tttgattcaa aagcatctta ccaataagga taaatatcat atacatcgtt       2580
atgaaaatat tgctatgaga taataagcca catatgaatg ttgtatacaa ctttagggtt       2640
tacatttaat cctgaagtgt tacctccttt catgtctatt tacactattt tcccatttac       2700
taagtgggga gggggtctcc ttatatagtg cttcatcgtt aataagtcaa tacctgttgt       2760
tcctgggatg ttcttttttg tgcattaaaa acttcaaaat taaaaaaaaa aaaaaaaaaa       2820
aaaaaaaaaa aaaaaaaaaa ag                                                2842
```

<210> SEQ ID NO 19
<211> LENGTH: 243
<212> TYPE: PRT
<213> ORGANISM: Homo sapiens

<400> SEQUENCE: 19

```
Met Gln Phe Arg Leu Phe Ser Phe Ala Leu Ile Ile Leu Asn Cys Met
1               5                   10                  15

Asp Tyr Ser His Cys Gln Gly Asn Arg Trp Arg Ser Lys Arg Ala
            20                  25                  30

Ser Tyr Val Ser Asn Pro Ile Cys Lys Gly Cys Leu Ser Cys Ser Lys
        35                  40                  45

Asp Asn Gly Cys Ser Arg Cys Gln Gln Lys Leu Phe Phe Phe Leu Arg
    50                  55                  60

Arg Glu Gly Met Arg Gln Tyr Gly Glu Cys Leu His Ser Cys Pro Ser
65                  70                  75                  80

Gly Tyr Tyr Gly His Arg Ala Pro Asp Met Asn Arg Cys Ala Arg Cys
                85                  90                  95

Arg Ile Glu Asn Cys Asp Ser Cys Phe Ser Lys Asp Phe Cys Thr Lys
            100                 105                 110

Cys Lys Val Gly Phe Tyr Leu His Arg Gly Arg Cys Phe Asp Glu Cys
        115                 120                 125

Pro Asp Gly Phe Ala Pro Leu Glu Glu Thr Met Glu Cys Val Glu Gly
    130                 135                 140

Cys Glu Val Gly His Trp Ser Glu Trp Gly Thr Cys Ser Arg Asn Asn
145                 150                 155                 160

Arg Thr Cys Gly Phe Lys Trp Gly Leu Glu Thr Arg Thr Arg Gln Ile
                165                 170                 175

Val Lys Lys Pro Val Lys Asp Thr Ile Pro Cys Pro Thr Ile Ala Glu
            180                 185                 190

Ser Arg Arg Cys Lys Met Thr Met Arg His Cys Pro Gly Gly Lys Arg
        195                 200                 205

Thr Pro Lys Ala Lys Glu Lys Arg Asn Lys Lys Lys Arg Lys Leu
    210                 215                 220

Ile Glu Arg Ala Gln Glu Gln His Ser Val Phe Leu Ala Thr Asp Arg
225                 230                 235                 240

Ala Asn Gln
```

<210> SEQ ID NO 20
<211> LENGTH: 2165
<212> TYPE: DNA
<213> ORGANISM: Homo sapiens

<400> SEQUENCE: 20

```
gcggccgccc cggcggctcc tggaaccccg gttcgcggcg atgccagcca ccccagcgaa      60
```

-continued

| | | | |
|---|---|---|---|
| gccgccgcag ttcagtgctt ggataatttg aaagtacaat agttggtttc cctgtccacc | 120 |
| cgccccactt cgcttgccat cacagcacgc ctatcggatg tgagaggaga agtcccgctg | 180 |
| ctcgggcact gtctatatac gcctaacacc tacatatatt ttaaaaacat taaatataat | 240 |
| taacaatcaa agaaagagg agaaaggaag ggaagcatta ctgggttact atgcacttgc | 300 |
| gactgatttc ttggcttttt atcattttga actttatgga atacatcggc agccaaaacg | 360 |
| cctcccgggg aaggcgccag cgaagaatgc atcctaacgt tagtcaaggc tgccaaggag | 420 |
| gctgtgcaac atgctcagat tacaatggat gtttgtcatg taagcccaga ctattttttg | 480 |
| ctctggaaag aattggcatg aagcagattg gagtatgtct ctcttcatgt ccaagtggat | 540 |
| attatggaac tcgatatcca gatataaata agtgtacaaa atgcaaagct gactgtgata | 600 |
| cctgttttcaa caaaaatttc tgcacaaaat gtaaaagtgg attttactta caccttggaa | 660 |
| agtgccttga caattgccca aagggttgg aagccaacaa ccatactatg gagtgtgtca | 720 |
| gtattgtgca ctgtgaggtc agtgaatgga atccttggag tccatgcacg aagaagggaa | 780 |
| aaacatgtgg cttcaaaaga gggactgaaa cacgggtccg agaataata cagcatcctt | 840 |
| cagcaaaggg taacctgtgt cccccaacaa atgagacaag aaagtgtaca gtgcaaagga | 900 |
| agaagtgtca gaagggagaa cgaggaaaaa aaggaaggga gaggaaaaga aaaaaaccta | 960 |
| ataaaggaga aagtaaagaa gcaataccttg acagcaaaag tctggaatcc agcaaagaaa | 1020 |
| tcccagagca acgagaaaac aaacagcagc agaagaagcg aaaagtccaa gataaacaga | 1080 |
| aatcggtatc agtcagcact gtacactaga gggttccatg agattattgt agactcatga | 1140 |
| tgctgctatc tcaaccagat gcccaggaca ggtgctctag ccattaggac acaaatggga | 1200 |
| catgtcagtt attgctctgt ctaaacaaca ttcccagtag ttgctatatt cttcatacaa | 1260 |
| gcatagttaa caacaaagag ccaaaagatc aagaaggga tactttcaga tggttgtctt | 1320 |
| gtgtgcttct ctgcattttt aaaagacaag acattcttgt acatattatc aataggctat | 1380 |
| aagatgtaac aacgaaatga tgacatctgg agaagaaaca tcttttcctt ataaaaatgt | 1440 |
| gttttcaagc tgttgtttta agaagcaaaa gatagttctg caaattcaaa gatacagtat | 1500 |
| cccttcaaaa caaataggag ttcagggaag agaaacatcc ttcaaaggac agtgttgttt | 1560 |
| tgaccgggag atctagagag tgctcagaat tagggcctgg catttggaat cacaggattt | 1620 |
| atcatcacag aaacaactgt tttaagatta gttccatcac tctcatcctg tatttttata | 1680 |
| agaaacacaa gagtgcatac cagaattgaa tataccatat gggattggag aaagacaaat | 1740 |
| gtggaagaaa tcatagagct ggagactact tttgtgcttt acaaaactgt gaaggattgt | 1800 |
| ggtcacctgg aacaggtctc caatctatgt tagcactatg tggctcagcc tctgttaccc | 1860 |
| cttggattat atatcaacct gtaaacatgt gcctgtaact tacttccaaa aacaaaatca | 1920 |
| tacttattag aagaaaattc tgattttata gaaaaaaaat agagcaagga gaatataaca | 1980 |
| tgtttgcaaa gtcatgtgtt ttcttttctca atgagggaaa aacaattta ttacctgctt | 2040 |
| aatggtccac ctggaactaa aagggatact attttctaac aaggtatatc tagtagggga | 2100 |
| gaaagccacc acaataaata tatttgttaa tagttttttca aaaaaaaaa aaaaaaaaa | 2160 |
| aaaaa | 2165 |

<210> SEQ ID NO 21
<211> LENGTH: 272
<212> TYPE: PRT
<213> ORGANISM: Homo sapiens

<400> SEQUENCE: 21

```
Met His Leu Arg Leu Ile Ser Trp Leu Phe Ile Ile Leu Asn Phe Met
1               5                   10                  15

Glu Tyr Ile Gly Ser Gln Asn Ala Ser Arg Gly Arg Gln Arg Arg
            20                  25                  30

Met His Pro Asn Val Ser Gln Gly Cys Gln Gly Cys Ala Thr Cys
        35                  40                  45

Ser Asp Tyr Asn Gly Cys Leu Ser Cys Lys Pro Arg Leu Phe Phe Ala
    50                  55                  60

Leu Glu Arg Ile Gly Met Lys Gln Ile Gly Val Cys Leu Ser Ser Cys
65                  70                  75                  80

Pro Ser Gly Tyr Tyr Gly Thr Arg Tyr Pro Asp Ile Asn Lys Cys Thr
                85                  90                  95

Lys Cys Lys Ala Asp Cys Asp Thr Cys Phe Asn Lys Asn Phe Cys Thr
            100                 105                 110

Lys Cys Lys Ser Gly Phe Tyr Leu His Leu Gly Lys Cys Leu Asp Asn
            115                 120                 125

Cys Pro Glu Gly Leu Glu Ala Asn Asn His Thr Met Glu Cys Val Ser
    130                 135                 140

Ile Val His Cys Glu Val Ser Glu Trp Asn Pro Trp Ser Pro Cys Thr
145                 150                 155                 160

Lys Lys Gly Lys Thr Cys Gly Phe Lys Arg Gly Thr Glu Thr Arg Val
                165                 170                 175

Arg Glu Ile Ile Gln His Pro Ser Ala Lys Gly Asn Leu Cys Pro Pro
            180                 185                 190

Thr Asn Glu Thr Arg Lys Cys Thr Val Gln Arg Lys Lys Cys Gln Lys
            195                 200                 205

Gly Glu Arg Gly Lys Gly Arg Glu Arg Lys Arg Lys Pro Asn
    210                 215                 220

Lys Gly Glu Ser Lys Glu Ala Ile Pro Asp Ser Lys Ser Leu Glu Ser
225                 230                 235                 240

Ser Lys Glu Ile Pro Glu Gln Arg Glu Asn Lys Gln Gln Lys Lys
            245                 250                 255

Arg Lys Val Gln Asp Lys Gln Lys Ser Val Ser Val Ser Thr Val His
            260                 265                 270
```

<210> SEQ ID NO 22
<211> LENGTH: 2722
<212> TYPE: DNA
<213> ORGANISM: Homo sapiens

<400> SEQUENCE: 22

```
cacagcagcc cccgcgcccg ccgtgccgcc gccgggacgt ggggcccttg ggccgtcggg      60
ccgcctgggg agcgccagcc cggatccggc tgcccagatg cgggcgccac tctgcctgct    120
cctgctcgtc gccacgccg  tggacatgct cgccctgaac cgaaggaaga agcaagtggg    180
cactggcctg ggggcaact  gcacaggctg tatcatctgc tcagaggaga acggctgttc    240
cacctgccag cagaggctct tcctgttcat ccgccgggaa ggcatccgcc agtacggcaa    300
gtgcctgcac gactgtcccc ctgggtactt cggcatccgc ggccaggagg tcaacaggtg    360
caaaaaatgt ggggccactt gtgagagctg cttcagccag gacttctgca tccggtgcaa    420
gaggcagttt tacttgtaca gggaagtg   tctgccccac ctgcccgccgg gcactttggc    480
ccaccagaac acacgggagt gccagggga gtgtgaactg ggtccctggg gcggctggag    540
cccctgcaca cacaatggaa agacctgcgg ctcggcttgg ggcctggaga gccgggtacg    600
```

```
agaggctggc cgggctgggc atgaggaggc agccacctgc caggtgcttt ctgagtcaag    660
gaaatgtccc atccagaggc cctgcccagg agagaggagc ccggccaga agaagggcag    720 gaaggaccgg cgcccacgca aggacaggaa gctggaccgc aggctggacg tgaggccgcg    780
ccagcccggc ctgcagccct gaccgccggc tctcccgact ctctggtcct agtcctcggc    840
ccctgcacac ctcctcctgc tccttctcct cctctcctct tactctttct cctctgtctt    900
ctccatttgt cctctctttc tttccaccct tctatcattt ttctgtcagt ctaccttccc    960 tttcttttc ttttttattt cctttatttc ttccacctcc attctcctct cctttctccc    1020
tccctccttc ccttccttcc tcttctttct cacttatctt ttatctttcc ttttctttct    1080
tcctgtgttt cttcctgtcc ttcaccgcat ccttctctct ctccctcctc ttgtctccct    1140
ctcacacaca ctttaagagg gaccatgagc ctgtgccctc ccctgcagct ttctctatct    1200
acaacttaaa gaaagcaaac atcttttccc aggcctttcc ctgaccccat ctttgcagag    1260
aaagggtttc cagagggcaa agctgggaca cagcacaggt gaatcctgaa ggccctgctt    1320
ctgctctggg ggaggctcca ggaccctgag ctgtgagcac ctggttctct ggacagtccc    1380
cagaggccat ttccacagcc ttcagccacc agccaccccg aggagctggc tggacaaggc    1440
tccagggctt ccagaggcct ggcttggaca cctcccccag ctggccgtgg agggtcacaa    1500
cctggcctct gggtgggcag ccagccctgg agggcatcct ctgcaagctg cctgccaccc    1560
tcatcggcac tcccccacag gcctccctct catgggttcc atgccccttt tcccaagcc    1620 ggatcaggtg agctgtcact gctgggggat ccacctgccc agcccagaag aggccactga    1680
aacggaaagg aaagctgaga ttatccagca gctctgttcc ccacctcagc gcttcctgcc    1740
catgtgggga acaggtctg agaaggaagg ggcttgccca gggtcacaca ggaagccttc    1800
aggctctgct tctgcctgat ggctctgctc agcacattca cggtggagag gagaatttgg    1860
gggtcacttg aggggggaaa tgtagggaat tgtgggtggg gagcaaggga agatccgtgc    1920
actcgtccac acccaccacc acactcgctg acacccaccc ccacacgctg acacccaccc    1980
ccacacttgc ccacacccat caccgcactc gcccacaccc accaccacac tgccccacac    2040
ccaccaccac actcccccac acccaccacc acactcgccc acaccaccaa ccagtgactt    2100
gagcatctgt gcttcgctgt gacgcccctc gccctaggca ggaacgacgc tgggaggagt    2160
ctccaggtca gacccagctt ggaagcaagt ctgtcctcac tgcctatcct tctgccatca    2220
taacaccccc ttcctgctct gctccccgga atcctcagaa acgggatttg tatttgccgt    2280
gactggttgg cctgaacacg tagggctccg tgactggaca aggaatgggc aggagaagca    2340
agagtcggag ctccaagggg cccaggggtg gcctggggaa ggaagatggt cagcaggctg    2400
ggggagaggc tctaggtgat gaaatattac attcccgacc ccaagagagc acccaccctc    2460
agacctgccc tccacctggc agctggggag ccctggcctg aaccccccc tcccagcagg    2520 cccaccctct ctctgacttc cctgctctca cctcccgag aacagctaga gccccctcct    2580
ccgcctggcc aggccaccag cttctcttct gcaaacgttt gtgcctctga aatgctccgt    2640
tgttattgtt tcaagaccct aacttttttt taaaactttc ttaataaagg gaaaagaaac    2700
ttgtaaaaaa aaaaaaaaaa aa                                            2722
```

<210> SEQ ID NO 23
<211> LENGTH: 234
<212> TYPE: PRT
<213> ORGANISM: Homo sapiens

```
<400> SEQUENCE: 23

Met Arg Ala Pro Leu Cys Leu Leu Leu Val Ala His Ala Val Asp
1               5                   10                  15

Met Leu Ala Leu Asn Arg Arg Lys Lys Gln Val Gly Thr Gly Leu Gly
                20                  25                  30

Gly Asn Cys Thr Gly Cys Ile Ile Cys Ser Glu Glu Asn Gly Cys Ser
            35                  40                  45

Thr Cys Gln Gln Arg Leu Phe Leu Phe Ile Arg Arg Glu Gly Ile Arg
    50                  55                      60

Gln Tyr Gly Lys Cys Leu His Asp Cys Pro Pro Gly Tyr Phe Gly Ile
65                  70                      75                  80

Arg Gly Gln Glu Val Asn Arg Cys Lys Lys Cys Gly Ala Thr Cys Glu
                85                  90                  95

Ser Cys Phe Ser Gln Asp Phe Cys Ile Arg Cys Lys Arg Gln Phe Tyr
            100                 105                 110

Leu Tyr Lys Gly Lys Cys Leu Pro Thr Cys Pro Pro Gly Thr Leu Ala
            115                 120                 125

His Gln Asn Thr Arg Glu Cys Gln Gly Glu Cys Glu Leu Gly Pro Trp
            130                 135                 140

Gly Gly Trp Ser Pro Cys Thr His Asn Gly Lys Thr Cys Gly Ser Ala
145                 150                 155                 160

Trp Gly Leu Glu Ser Arg Val Arg Glu Ala Gly Arg Ala Gly His Glu
                165                 170                 175

Glu Ala Ala Thr Cys Gln Val Leu Ser Glu Ser Arg Lys Cys Pro Ile
            180                 185                 190

Gln Arg Pro Cys Pro Gly Glu Arg Ser Pro Gly Gln Lys Lys Gly Arg
        195                 200                 205

Lys Asp Arg Arg Pro Arg Lys Asp Arg Lys Leu Asp Arg Arg Leu Asp
            210                 215                 220

Val Arg Pro Arg Gln Pro Gly Leu Gln Pro
225                 230
```

RSPONDINS AS MODULATORS OF ANGIOGENESIS AND VASCULOGENESIS

CROSS REFERENCE TO RELATED APPLICATIONS

The present application is a Continuation Application of co-pending application Ser. No. 14/870,846, filed Sep. 30, 2015, which is a Continuation Application of co-pending application Ser. No. 14/453,692, filed Aug. 7, 2014, now U.S. Pat. No. 9,226,963, which is a Divisional of co-pending application Ser. No. 14/048,225, filed Oct. 8, 2013, now U.S. Pat. No. 8,926,970, which is a Continuation Application of co-pending application Ser. No. 13/309,193, filed Dec. 1, 2011, now U.S. Pat. No. 8,580,736, which is a Divisional of co-pending National Stage application Ser. No. 12/311,921, filed Apr. 16, 2009, now U.S. Pat. No. 8,088,374, which claims priority from PCT Application No. PCT/EP2007/009105 filed Oct. 19, 2007, which in turn, claims priority from EP Application Serial No. 06 022 070.4, filed Oct. 20, 2006. Applicants claim the benefits of 35 U.S.C. § 120 as to the U.S. Non-Provisional applications and the PCT application, and priority under 35 U.S.C. § 119 as to the said EP application, and the entire disclosures of all applications are incorporated herein by reference in their entireties.

1. INTRODUCTION

The present invention relates to the use of Rspondin polypeptides, particularly Rspondin2 (Rspo2) or Rspondin3 (Rspo3) or Rspondin nucleic acids, or regulators or effectors or modulators of Rspondin respectively. The invention is based on the demonstration that Rspo3 and Rspo2 are angiogenesis promoters, and the identification of Rspo2 and 3 as positive regulators of vascular endothelial growth factor (VEGF). These results indicate a major role for Rspondins, particularly Rspo3 and/or Rspo2 in the signalling system during angiogenesis. The invention also relates to the use of Rspondin3 regulators or effectors or modulators, including agonists and antagonists, in the treatment of conditions, including cancer, by modulating angiogenesis and/or vasculogenesis.

2. BACKGROUND OF THE INVENTION

The Rspondin protein family is conserved among vertebrates and consists of the four related members Rspondin1-4 (Rspo1-4) (Chen et al., 2002, Mol. Biol. Rep. 29, 287-292, who called Rspo3 hPWTSR; Kamata et al., 2004, Biochim. Biophys. Anta. 1676, 51-62; Kazanskaya et al., 2004, Dev. Cell 7, 525-534; Kim et al., 2005, Science 309, 1256-1259; Kim et al., 2006, Cell Cycle 5, 23-26; Nam et al., 2006, J. Biol. Chem. 281, 13247-13257). Human Rspo1-4 were also described as Stem Cell Growth Factor Like Polypeptides, which are able to promote proliferation of hematopoietic stem cells (WO 01/77169; WO 01/07611). They were also designated as Futrin1-4 and identified as modulators of the Wnt signalling pathway (WO 2005/040418). The content of these documents is herein incorporated by reference and the amino acid and nucleic sequences of Rspondins 1-4 disclosed therein are specifically included herein.

The Rspo genes encode secreted proteins which can activate Wnt/b-catenin signalling, and Rspo2 promotes myogenesis via the Wnt/b-catenin signalling pathway in Xenopus (Kazanskaya et al., 2004, Dev. Cell 7, 525-534). Rspondin genes are widely coexpressed with Wnt genes in many regions during embryonic development, and Rspondin expression is positively regulated by Wnt signals (Kamata et al., 2004, Biochim. Biophys. Acta. 1676, 51-62; Kazanskaya et al., 2004, Dev. Cell 7, 525-534). Furthermore, it was reported that secreted human Rspo1 promotes proliferation of intestinal epithelium through stabilizing of b-catenin (Kim et al., 2005 Science 309, 1256-9). Mutation of mouse Rspo3 results in embryonic lethality and induces severe defects in the development of the placenta (Aoki et al., Dev Biol. 2007 301(1):218-26). However, no effect on blood vessel development was reported in this mutant model and, in contrast to the results disclosed herein, the embryos appeared to show no sign of haemorrhage, therefore there was no suggestion before the present invention that Rspondin, in particular Rspondin 2 or 3, played a significant role in angiogenesis and/or vasculogenesis.

Angiogenesis is likely to be regulated by polypeptide growth factors. Several polypeptides with in vitro endothelial cell growth promoting activity have been identified. Examples include acidic and basic fibroblastic growth factor, VEGF and placental growth factor.

VEGF is a key factor in vasculogenesis and angiogenesis and its signalling pathway an important target for pharmacological intervention (Ferrara 2005, Oncology 3:11-6; Rosen 2005, Oncologist 10:382-91).

3. SUMMARY OF THE INVENTION

The present invention relates to the use of Rspondin polypeptides or Rspondin nucleic acids, or regulators or effectors or modulators of Rspondin polypeptides or Rspondin nucleic acids. The invention is based on the demonstration that Rspo3 and Rspo2 are vasculogenesis and angiogenesis promoters. Further, they induce endothelial cell growth and have been identified as positive regulators of VEGF.

The results indicate a major role for Rspondins polypeptides, particularly Rspo2 and/or Rspo3 in the signalling system during angiogenesis and/or vasculogenesis.

Rspondin polypeptides (e.g. Rspo2 or Rspo3), Rspondin nucleic acids, and agonists of Rspondin, are suitable in the treatment of conditions wherein said treatment involves promoting angiogenesis and/or vasculogenesis Antagonists of Rspondin polypeptides (e.g. of Rspo2 or Rspo3) or of Rspondin nucleic acids, are suitable in the treatment of conditions wherein said treatment involves inhibiting angiogenesis and/or vasculogenesis.

The invention also relates to the use of Rspondin polypeptides, Rspondin nucleic acids and regulators or effectors or modulators of Rspondin for diagnostic applications, particularly for the diagnosis or monitoring of angiogenesis-and/or vasculogenesis-associated processes, conditions and disorders.

Further, the invention refers to cells and transgenic non-human animals exhibiting modified, e.g. increased or decreased Rspondin, particularly Rpo2 and/or Rspo3, expression.

Rspondin polypeptides and Rspondin nucleic acids and cells or transgenic animals may be used in screening procedures in order to identify and/or characterize effectors of angiogenesis and/or vasculogenesis.

4. BRIEF DESCRIPTION OF THE FIGURES

FIG. 1: Rspo3 is necessary for the blood vessel cell development in *Xenopus tropicalis*. *Xenopus tropicalis* embryos were injected at the 4 cell stage with control or Rspo3 morpholino antisense oligonucleotides (Mo) as indicated. Embryos were fixed at tailbud stage and in situ hybridization for markers of blood (α-globin, SCL, Mead et al., 1998, Development 125, 2611-2620) or forming blood vessels (msr, Devic et al., Mech Dev. 1996; 59, 129-40) was carried out. Note the expansion of blood markers and inhibition of msr in Rspo3 Mo-treated embryos.

Figure 2:
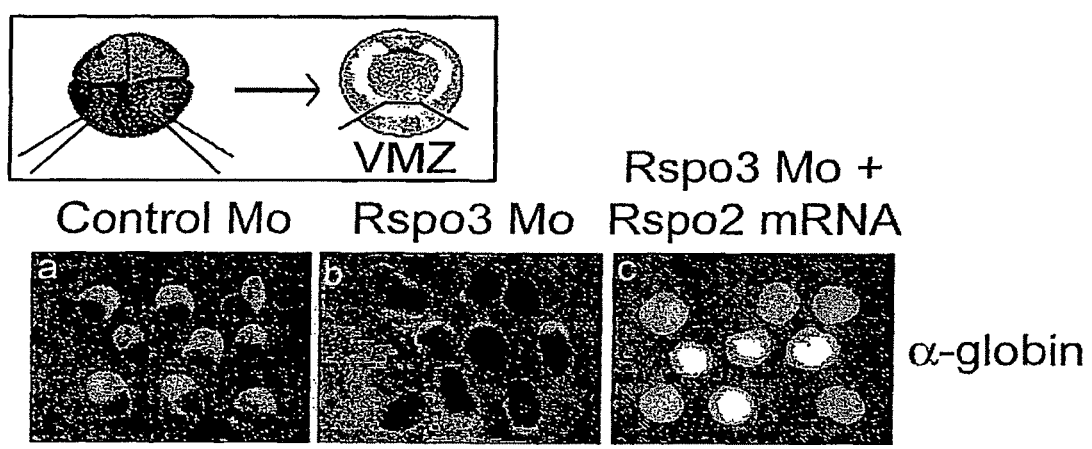

FIG. 2: Demonstration of the specificity of Rspo3 morpholino antisense oligonucleotides. *Xenopus tropicalis* embryos were injected in two ventral blastomers at the 4-8 cells stage with Rspo3 morpholino antisense oligonucleotides (Mo) with and without *Xenopus laevis* Rspo2 mRNA as indicated. At gastrula stage (stage 10) ventral marginal zones (VMZ) were excised and cultured until sibling embryos reached stage 28. VMZs were fixed and processed for whole mount in situ hybridization for the blood marker α-globin. Note rescue of Rspo3 Mo-induced expansion of α-globin by Rspo2 mRNA. This rescue shows the specificity of the morpholino phenotype.

Figure 3:
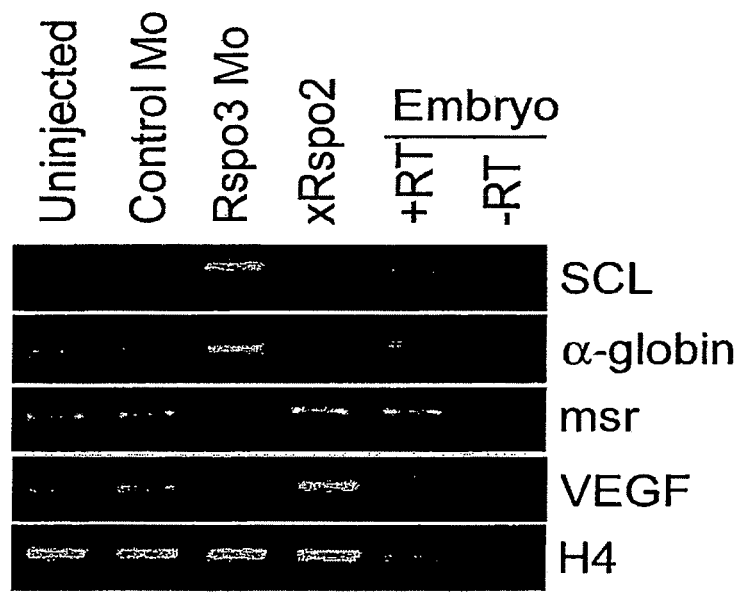

FIG. 3: Rspo3 is necessary and sufficient for promoting blood vessel cell development in *Xenopus tropicalis*. *Xenopus tropicalis* embryos were injected at the 4 cells stage with control or Rspo3 morpholino antisense oligonucleotides (Mo) or *Xenopus laevis* Rspo2 mRNA as indicated. At gastrula stage the ventral marginal zone was excised and cultivated in isolation until stage 28. RT-PCR analysis was carried out for the indicated marker genes. H4, histone 4 for normalization. –RT, minus reverse transcriptase control. Note that Mo inhibition of Rspo3 inhibits blood vessel marker VEGF and msr expression and induces the blood markers α-globin and SCL.

Figure 4:
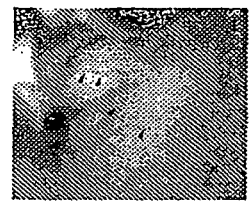

FIG. 4: Expression of. Rspo3 in vasculature of mouse embryos. In situ hybridisation of Rspo3 in E 10.5 mouse embryo is shown. Arrowheads point to expression in embryonic blood vessels.

Figure 5:
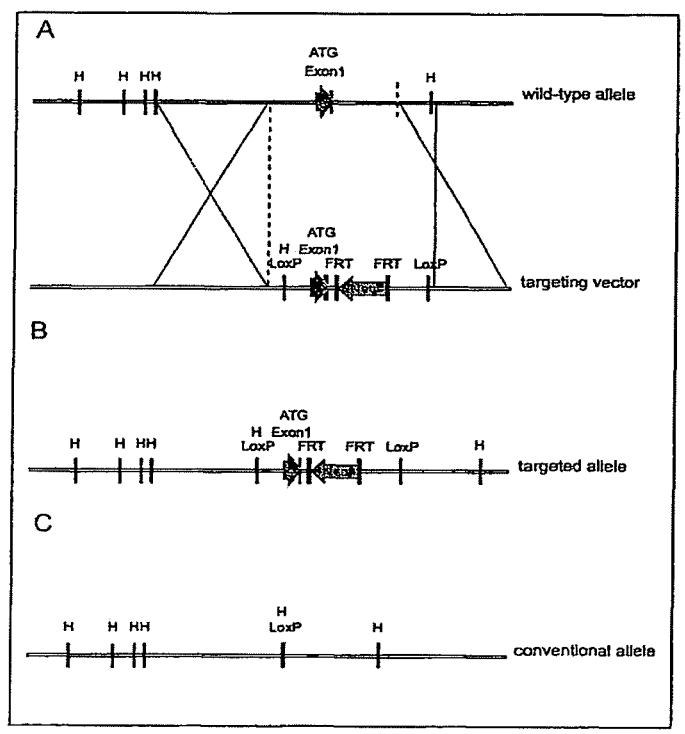

FIG. 5: Targeted mutagenesis of murine Rspo3. (A) Genomic structure of Rspo3 and targeting vector used for homologous recombination is ES cells. (B) Targeted allele before and (C) after elimination of neomycine selectable marker gene using Flp recombinase.

Figure 6:
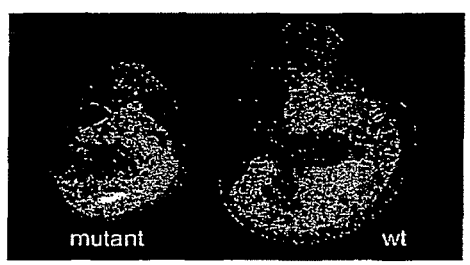

FIG. 6: Rspo3 mutant mice show internal bleeding. Photographs of wild-type (wt) and Rspo3–/– embryos (mutant) mice at E10.5. Note haemorrhages in the mutant mouse, indicative of failure of blood vessel formation.

Figure 7:
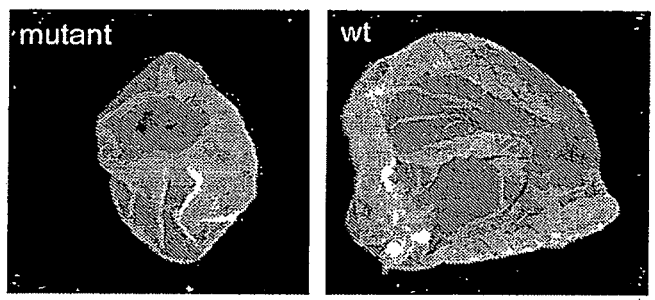

FIG. 7: Rspo3 mutant mice show reduced blood vessel formation. Wild-type (wt) and Rspo3–/– (mutant) yolk sacs of E 10.5 embryos are shown. Note pale yolk sac in mutant.

Figure 8:
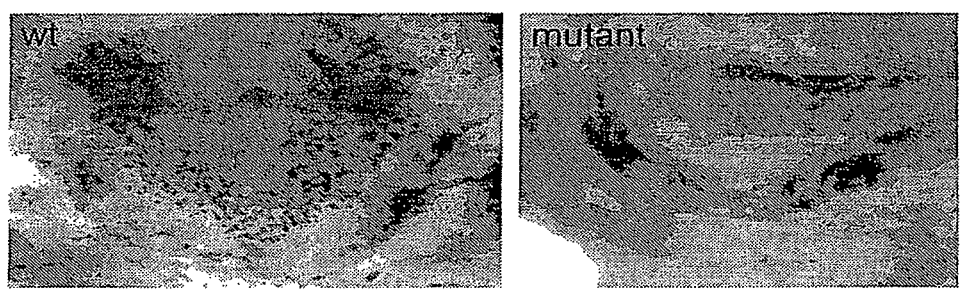

FIG. 8: Rspo3 mutant mice lose VEGF expression. Whole mount in situ hybridization for VEGF is shown in placentas of wild-type (wt) and Rspo3–/– embryos (mutant) of E 9.5.

Figure 9:
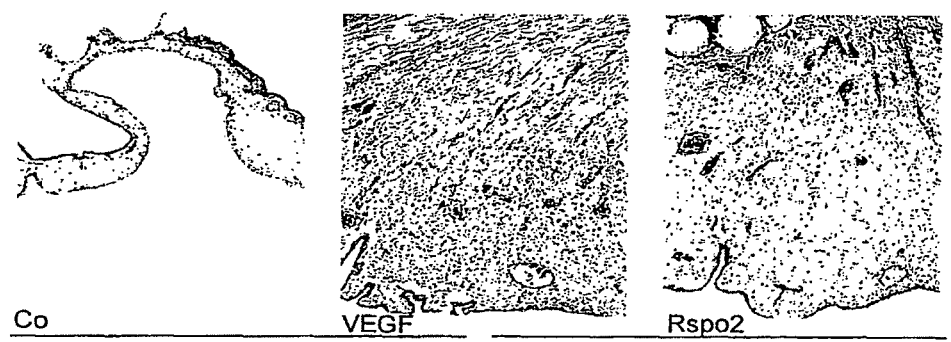

FIG. 9: Rspo2 induces angiogenesis in the chicken chorioallantoic membrane (CAM) assay.

Figure 10:
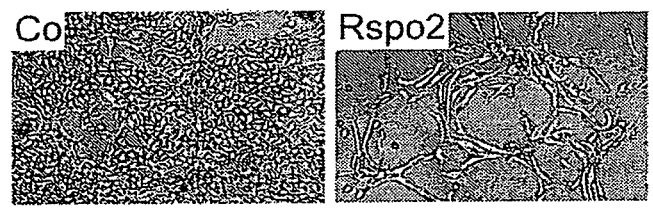

FIG. 10: Rspo2 induces tube formation in endothelial cells. Control or *Xenopus laevis* Rspo2 conditioned medium was applied to human endothelial cells (HDMEC) for 5 days. Note induction of morphogenesis indicative of tube formation, as is characteristic during angiogenesis.

Figure 11:
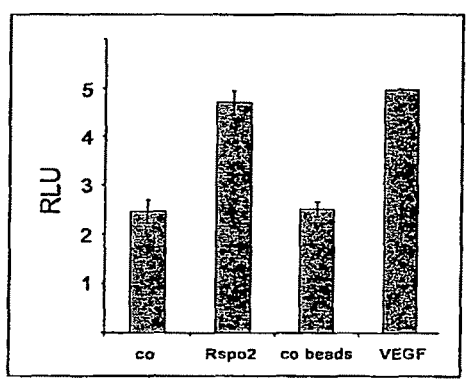

FIG. 11: Rspo2 induces endothelial cell growth. Control or *Xenopus laevis* Rspo2 conditioned medium or 0.5 ng/ml VEGF was applied to human endothelial cells (HUVEC) for 2 days and cell proliferation was assayed using a commercial kit (Roche).

5. DESCRIPTION OF THE INVENTION

5.1 Definitions

As used herein the term 'Rspondin polypeptides' according to the present invention refers to members of the Rspondin family which may be derived from mammalian or other vertebrate organisms. The Rspondin protein family consists of the four related members Rspondin1-4 (Rspo1-4).

Preferably, the Rspondin polypeptide is a human Rspondin, e.g. human Rspondin1, 2, 3 or 4. More preferably, the Rspondin polypeptide is an Rspondin2 or 3 polypeptide, particularly a human Rspondin2 or 3 polypeptide. The amino acid sequences of human Rspondin polypeptides 1, 2, 3 and 4 are shown in WO 2005/040418, the content of which is herein incorporated by reference. Further examples of Rspondin polypeptides are Rspondins from *Xenopus*, e.g. *Xenopus tropicalis* and *Xenopus laevis* or from *Mus musculus*.

Further sequences for human Rspondin nucleic acid and amino acid sequences are as follows: Human Rspondin 1 nucleic acid sequence (NM_001038633, SEQ ID NO: 16), amino acid sequence (ABA54597, SEQ ID NO: 17), human Rspondin 2 nucleic acid sequence (NM_178565, SEQ ID NO: 18), amino acid sequence (NP_848660, SEQ ID NO: 19), human Rspondin 3 nucleic acid sequence (NM_032784, SEQ ID NO: 20), amino acid sequence (NP_116173, SEQ ID NO: 21), human Rspondin 4 nucleic acid sequence (NM_001029871, SEQ ID NO: 22), amino acid sequence (NP_001025042, SEQ ID NO: 23).

Rspondin polypeptides are further defined herein as polypeptides that show at least 40%, preferably at least 60%, more preferably at least 80%, at least 90%, at least 95%, at least 98% or at least 99% sequence identity at the amino acid level to the respective human Rspondin polypeptide over its entire length (Kazanskaya et al., 2004, Dev. Cell 7, 525-534). Further, Rspondin polypeptides according to the invention are preferably characterized as having at least one biological activity selected from i induction of angiogenesis in the CAM assay,
ii induction of tube formation in endothelial cells,
iii induction of endothelial cell growth, particularly growth of human endothelial cells, and
iv induction of VEGF expression.

The term 'polypeptide' includes to full-length proteins, proteinaceous molecules, fragments of proteins, fusion proteins, peptides, oligopeptides, variants, derivatives, analogs or functional equivalents thereof.

The term 'functionally equivalent to Rspondin' as used herein refers to a protein which induces angiogenesis and/or VEGF expression. The gene product itself may contain deletions, additions or substitutions of amino acid residues within the Rspondin, e.g. Rspo2 or Rpo3 sequence, which result in a silent change thus retaining significant signal transducing capacity thus producing a functionally equivalent Rspondin. Such amino acid substitutions may be made on the basis of similarity in polarity, charge, solubility, hydrophobicity, hydrophilicity, and/or the amphipatic nature of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, analine; asparagine, glutamine; serine, threonine; phenylalanine, tyrosine.

As used herein the term "'Rspondin nucleic acid' refers to nucleic acid sequences that encode members of the Rspondin family and which may be derived from mammalian or other vertebrate organisms. Preferably, the Rspondin nucleic encodes a human Rspondin, e.g. human Rspondin1, 2, 3 or 4. More preferably, the Rspondin nucleic acid encodes an Rspondin2 or 3 polypeptide, particularly it encodes a human Rspondin2 or 3 polypeptide. The nucleic acid sequences of human Rspondin 1, 2, 3 and 4 are shown in WO 2005/040418, the content of which is herein incorporated by reference. Further examples of Rspondin nucleic acids are those which encode the Rspondins from *Xenopus*, e.g. *Xenopus tropicalis* and *Xenopus laevis* or from *Mus musculus*.

Rspondin nucleic acids are further defined herein as molecules selected from
- (a) nucleic acid molecules encoding Rspondin polypeptides, e.g a human Rspondin, particularly Rspo2 and/or Rspo3,
- (b) nucleic acid molecules which hybridize under stringent conditions to a nucleic acid molecule of (a) and/or a nucleic acid molecule which is complementary thereto,
- (c) nucleic acid molecules which encode the same polypeptide as a nucleic acid molecule of (a) and/or (b), and
- (d) nucleic acid molecules which encode a polypeptide which is at least 40%, preferably at least 60%, more preferably at least 80%, and most preferably at least 90% identical to a polypeptide encoded by a nucleic acid molecule of (a) over its entire length.

The nucleic acid molecules may be e.g. DNA molecules or RNA molecules.

Nucleic acid molecules which may be used in accordance with the invention may include deletions, additions or substitutions of different nucleotide residues resulting in a sequence that encodes the same or a functionally equivalent gene product.

As used herein, the terms 'regulators' or 'effectors' or 'modulators' of Rspondin polypeptides or nucleic acids are used interchangeably herein and any of the above may be used to refer to antibodies, peptides, low molecular weight organic or inorganic molecules and other sources of potentially biologically active materials capable of modulating Rspondin polypeptides, e.g. Rspo2 and/or Rspo3 signal transduction or capable of modulating Rspondin polypeptide activity or capable of modulating Rspondin expression to promote (agonists) or inhibit (antagonists) angiogenesis and/or vasculogenesis. Said regulators, effectors or modulators can be naturally occurring or synthetically produced.

As used herein, the term 'compound capable of binding to Rspondin' refers to a naturally occurring or synthetically produced regulator, effector or modulator of Rspondin' which interacts with an Rspondin polypeptide. Examples of such compounds are (i) a natural partner, e.g. receptor of an Rspondin; (ii) a naturally occurring molecule which is part of the signalling complex; and/or a naturally occurring signalling molecule produced by other cell types; (iii) naturally occurring or synthetically produced antibody. The term 'compound' is used herein in the context of a 'test compound' or a 'drug candidate compound.

As used herein the term 'agonist of Rspondin' refers to regulators or effectors or modulators of Rspondin that activate the intracellular response of Rspondin and thus promote angiogenesis and/or vasculogenesis.

As used herein, the term 'antagonist of Rspondin' refers to regulators or effectors or modulators of Rspondin polypeptides or Rspondin nucleic acids that inhibit, decrease or prevent the intracellular response of Rspondin polypeptides or Rspondin nucleic acids and thus inhibit, decrease or prevent angiogenesis and/or vasculogenesis.

Examples of suitable antagonists are mutated forms of Rspondin, having a dominant negative effect, Rspondin-binding polypeptides, e.g. anti-Rspondin antibodies including recombinant antibodies or antibody fragments containing at least one Rspondin binding site. Further examples of Rspondin antagonists are nucleic acids capable of inhibiting Rspondin translation, transcription, expression and/or activity, e.g. aptamers, antisense molecules, ribozymes or nucleic acid molecules capable of RNA interference such as siRNA molecules including nucleic acid analogs such as peptidic nucleic acids or morpholino nucleic acids. Such nucleic acids may bind to or otherwise interfere with Rspondin nucleic acids.

As used herein, the term 'antibody' or 'antibodies' includes but is not limited to recombinant polyclonal, monoclonal, chimeric, humanized, or single chain antibodies or fragments thereof including Fab fragments, single chain fragments, and fragments produced by an Fab expression library. Neutralizing antibodies i.e., those which compete for the VEGF binding site of an Rspondin are especially preferred for diagnostics and therapeutics.

As used herein, the term 'vasculogenesis' refers to the formation and spreading of blood vessels.

As used herein, the term 'angiogenesis' relates to a process which involves the vascularisation of a tissue, in particular, the proliferation, migration and infiltration of vascular endothelial cells and the growth and the development of new capillary blood vessels.

As used herein, the term 'treating' or 'treatment' refers to an intervention performed with the intention of preventing the development or altering the pathology of, and thereby alleviating a disorder, disease or condition, including one or more symptoms of such disorder or condition. Accordingly, 'treating' refers to both therapeutic treatment and prophylactic or preventative measures. Those in need of treating include those already with the disorder as well as those in which the disorder is to be prevented. The related term 'treatment', as used herein, refers to the act of treating a disorder, symptom, disease or condition, as the term 'treating' is defined above.

As used herein the term "conditions where treatment involves inhibiting angiogenesis and/or vasculogenesis" specifically includes (without limitation) conditions such as tumor growth, e.g. solid tumor growth and metastatic activity, atherosclerosis, stenosis, restenosis, retinopathy, macular degeneration, psoriasis and rheumatoid arthritis.

As used herein, the term 'Conditions where treatment involves promoting angiogenesis- &/or vasculogenesis" specifically includes (without limitation) conditions such as wound healing, tissue and organ regeneration or development, vasculodegenerative processes (e.g. critical limb- or brain ischemia, ischemic heart disease), embryonic development, and reproductive processes, e.g. female reproduction processes, such as follicle development in the corpus luteum during ovulation and placental growth during pregnancy.

As used herein, the term "tumor" refers to a malignant new growth that arises from epithelium, found in skin or, more commonly, the lining of body organs, for example, breast, prostate, lung, kidney, pancreas, stomach or bowel. A tumor may also infiltrate into adjacent tissue and spread (metastasise) to distant organs, for example to bone, liver, lung or the brain. As used herein the term tumor includes both primary and metastatic tumor cell types, such as but not limited to, melanoma, lymphoma, leukaemia, fibrosarcoma, rhabdomyosarcoma, and mastocytoma and types of tissue carcinoma, such as but not limited to, colorectal cancer, prostate cancer, small cell lung cancer and non-small cell lung cancer, breast cancer, pancreatic cancer, bladder cancer, renal cancer, gastric cancer, gliobastoma, primary liver cancer and ovarian cancers.

5.2 Detailed Description of the Invention

Angiogenesis is required for a number of physiological processes ranging from wound healing, tissue and organ regeneration, embryonic development and reproductive processes such as follicle development in the corpus luteum during ovulation and placental formation during pregnancy. Abnormal proliferation of blood vessels is an important component of a variety of diseases such as rheumatoid arthritis, retinopathies, and psoriasis, these diseases (and related conditions) are referred to herein as "conditions where treatment involves inhibiting angiogenesis and/or vasculogenesis". Angiogenesis is also an important factor in the growth and metastatic activity of solid tumors that rely on vascularization. Therefore, inhibitors of angiogenesis may be used therapeutically for the treatment of diseases resulting from or accompanied by abnormal growth of blood vessels and for treatments of malignancies involving growth and spread of solid tumors.

The present invention relates to the use of Rspondin polypeptides, Rspondin nucleic acids and regulators or effectors or modulators of Rspondin polypeptides or Rspondin nucleic acids.

A first aspect of the present invention relates to the use of an Rspondin polypeptide, an Rspondin nucleic acid or an Rspondin agonist for the manufacture of an angiogenesis and/or vasculogenesis-promoting medicament.

A further aspect of the invention relates to the use of an Rspondin antagonist for the manufacture of an angiogenesis and/or vasculogenesis-inhibiting medicament.

A further aspect of the invention refers to methods and reagents for the diagnosis or monitoring of angiogenesis- and/or vasculogenesis-associated processes, conditions or disorders, comprising determining the amount, activity and/or expression of an Rspondin polypeptide or an Rspondin nucleic acid in a sample. In a particular embodiment of the present invention, the amount, activity and/or expression of an Rspondin polypeptide or an Rspondin nucleic acid in said sample is compared to the amount, activity and/or expression of said Rspondin polypeptide or Rspondin nucleic acid in a control sample.

Still a further aspect of the invention refers to recombinant cells and transgenic non-human animals exhibiting modified, e.g. increased or decreased Rspondin polypeptide expression.

Another aspect of the invention relates to the use of Rspondin polypeptides, Rspondin nucleic acids, cells and transgenic non-human animals to evaluate and screen test compounds for their ability to modulate, e.g. stimulate or inhibit angiogenesis- and/or vasculogenesis-associated processes, conditions or disorders. Such regulators of Rspondins may be used therapeutically. For example, agonists of Rspondins, e.g. Rspo2 and/or Rspo3 may be used in processes such as wound healing; in contrast, antagonists of Rspo3 may be used in the treatment of tumors that rely on vascularization for growth.

The invention is based, in part, on results from in situ-hybridization indicating that Rspo3 is expressed in the embryonic vasculature. The invention is also based on the discovery that expression of Rspo3 promotes endothelial cell differentiation, proliferation and morphogenesis, while inhibition by antisense molecules in Xenopus embryos or targeted mutagenesis in knock out mice interferes with angiogenesis. The invention is also based on the discovery that Rspo3 is a positive regulator, which is both necessary and sufficient for expression of the key angiogenic factor VEGF.

Accordingly, inhibition of Rspondin molecules may be useful for treatment of diseases resulting from abnormal proliferation of blood vessels mediated by Rspondin, e.g. Rspo2 and/or Rspo3, and/or VEGF, in particular in the treatment of conditions where treatment involves inhibiting angiogenesis and/or vasculogenesis The present invention relates to Rspondin polypeptides, Rspondin nucleic acids or regulators or effectors or modulators of Rspondin.

According to the present invention, an Rspondin polypeptide or a Rspondin nucleic acid may be used for promoting angiogenesis and/or vasculogenesis, particularly for the manufacture of an angiogenesis- and/or vaculogenesis-promoting medicament.

This embodiment encompasses the prevention or treatment of a condition where treatment involves promoting angiogenesis and/or vasculogenesis.

Rspondin polypeptides or Rspondin nucleic acids may be used in human or veterinary medicine, either alone or in combination with a further medicament, e.g. a further angiogenesis- and/or vasculogenesis-promoting medicament such as a FGF, VEGF, PDGF, TNF or L-lysine.

A further aspect of this embodiment of the invention refers to a method for promoting angiogenesis in a cell or an organism comprising increasing the level, activity and/or expression of an Rspondin polypeptide. This method may be carried out in vitro or in vivo, e.g. for therapeutic applications.

Further, this embodiment of the invention encompasses a method for promoting angiogenesis comprising administering to a subject in need thereof a therapeutically effective dose of an Rspondin polypeptide or a Rspondin nucleic acid, wherein the subject is preferably human.

A different embodiment of the present invention refers to the use of an Rspondin antagonist for the manufacture of an angiogenesis- and/or vasculogenesis-inhibiting medicament. The Rspondin antagonist is preferably an Rspondin2 anti/or Rspondin3 antagonist.

This embodiment of the present invention encompasses the prevention or treatment of a condition where treatment involves inhibiting angiogenesis and/or vasculogenesis.

In this embodiment, the Rspondin antagonist may be used in human or veterinary medicine, alone or in combination with a further medicament. For example, the treatment of tumors may comprise the combined use of an Rspondin antagonist and an anti-tumor agent, e.g. a chemotherapeutic agent or an anti-tumor antibody, e.g. Bevacizumab, Endostatin, Thalidomide, Combrestatin A4, an anti VEGF antibody, SU 5416 or SU 6668.

Preferably, the nucleic acid molecules are recombinant DNA molecules that direct the recombinant expression of Rspondin polypeptides in appropriate host cells. Alternatively, nucleotide sequences which hybridize to portions of an Rspondin-coding sequence may also be used in nucleic acid amplification and/or hybridization assays, e.g. PCR, Southern and Northern blot analyses, etc.

Due to the inherent degeneracy of the genetic code, nucleic acid molecules which encode substantially the same or a functionally equivalent polypeptide, may be used in the practice of the invention for the cloning and expression of an Rspondin, e.g. Rspo2 or 3 protein. Such DNA sequences include those which are capable of hybridizing to the Xenopus, and murine and/or human Rspondin sequences under stringent conditions. Preferably, hybridization under stringent conditions means that after washing for 1 h with 1×SSC buffer and 0.1% SDS, preferably at 55° C., more preferably at 62° C., and most preferably at 68° C., particularly for 1 h in 0.2×SSC buffer and 0.1 SDS at 50° C., preferably at 55° C., more preferably at 62° C. and most preferably at 68° C., a positive hybridization signal is observed.

The nucleic acid molecules of the invention may be engineered in order to alter the Rspondin-coding sequence for a variety of purposes including but not limited to alterations which modify processing and/or expression of the gene product. For example, mutations may be introduced using techniques which are well known in the art, e.g. site-directed mutagenesis, to insert new restriction sites, to alter glycosylation patterns, phosphorylation, etc. For example, in certain expression systems such as yeast, host cells may over glycosylate the gene product. When using such expression systems it may be preferable to alter the Rspo2 or 3-coding sequence to eliminate any N-linked glycosylation site.

In another embodiment of the invention, the Rspondin nucleic acid sequence may be ligated to a heterologous sequence to encode a fusion protein. For example, for screening of peptide libraries it may be useful to encode a chimeric Rspondin protein expressing a heterologous epitope that is recognized by a commercially available antibody. A fusion protein may also be engineered to contain a cleavage site located between the Rspondin sequence and the heterologous protein sequence, so that the Rspondin portion can be cleaved away from the heterologous moiety.

In an alternative embodiment of the invention, the coding nucleic acid sequence can be synthesized in whole or in part, using chemical methods well known in the art. See, for example, Caruthers, et al., 1980, Nuc. Acids Res. Symp. Ser. 7: 215-233; Crea and Horn, 180, Nuc. Acids Res. 9(10): 2331; Matteucci and Caruthers, 1980, Tetrahedron Letters 21: 719; and Chow and Kempe, 1981, Nuc. Acids Res. 9(12): 2807-2817. Alternatively, the protein itself can be produced using chemical methods to synthesize the Rspondin amino acid sequence in whole or in part. For example, peptides can be synthesized by solid phase techniques, cleaved from the resin, and purified by preparative high performance liquid chromatography (e.g., see Creighton, 1983, Proteins Structures And Molecular Principles, W. H. Freeman and Co., N.Y. pp. 50-60). The composition of the synthetic peptides may be confirmed by amino acid analysis or sequencing (e.g., the Edman degradation procedure; see Creighton, 1983, Proteins, Structures and Molecular Principles, W. H. Freeman and Co., N.Y., pp. 34-49).

In order to express a biologically active Rspondin polypeptide, the nucleotide sequence coding for said polypeptide is inserted into an appropriate expression vector, i.e., a vector which contains the necessary elements for the transcription and translation of the inserted coding sequence. The Rspo gene products as well as host cells or cell lines transfected or transformed with recombinant expression vectors can be used for a variety of purposes. These include but are not limited to generating antibodies (i.e., monoclonal or polyclonal) that bind to Rspondin, including those that "neutralize" the activity of Rspondin.

Methods which are well known to those skilled in the art can be used to construct expression vectors containing the Rspondin-coding sequence and appropriate transcriptional/translational control signals. These methods include in vitro recombinant DNA techniques, synthetic techniques and in vivo recombination/genetic recombination. See, for example, the techniques described in Maniatis et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.

A variety of host-expression vector systems may be utilized to express the Rspondin-coding sequence. These include but are not limited to microorganisms such as bacteria transformed with recombinant bacteriophage DNA, plasmid DNA or cosmid DNA expression vectors containing the Rspondin-coding sequence; yeast celly transformed with recombinant yeast expression vectors containing the Rspondin-coding sequence; insect cell systems infected with recombinant virus expression vectors (e.g., baculovirus) containing the Rspo2 or 3-coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the Rspondin-coding sequence; or animal cell systems infected with recombinant virus expression vectors (e.g., adenovirus, vaccinia virus) including cell lines engineered to contain multiple copies of the Rspondin DNA either stably amplified (CHO/dhfr-) or unstably amplified in double-minute chromosomes (e.g., murine cell lines).

In an embodiment of the invention, Rspondin polypeptides, e.g. Rspo2 and/or Rspo3, Respondin nucleic acids, and/or cell lines or non-human transgenic animals that express an Rspondin may be used to screen for regulators or effectors or modulators of Rspondin that act as agonists or antagonists of angiogenesis or vasculogenesis. For example, antibodies capable of neutralizing the activity of Rspondin, e.g. Rspo3 in an endothelial proliferation assay, a chicken CAM assay and/or a Xenopus VMZ differentiation assay, may be used to inhibit Rspondin function. Additionally, anti-Rspo3 antibodies which mimic VEGF activity may be selected for pro-angiogenic applications, e.g. in wound healing. Alternatively, screening of peptide libraries or organic compounds with recombinantly expressed soluble Rspondin polypeptides or cell lines or transgenic non-human animals expressing an Rspondin polypeptide may be useful for identification of therapeutic molecules that function by modulating, e.g. inhibiting the biological activity of Rspondin and thus are suitable as angiogenesis and/or vasculogenesis regulators or effectors or modulators of Rspondin, e.g. antagonists of Rspondin.

In an embodiment of the invention, engineered cell lines and/or transgenic non-human animals which exhibit modified Rspondin expression, e.g. an increased or decreased expression of an Rspondin compared to wild-type cell lines or animals, may be utilized to screen and identify antagonists as well as agonists. Synthetic compounds, natural products, and other sources of potentially biologically active materials can be screened in a number of ways to identify regulators or effectors or modulators of Rspondin. The ability of a test compound to inhibit the activity of an Rspondin polypeptide may be measured using an endothelial proliferation assay, a chicken CAM assay and/or a Xenopus VMZ differentiation assay, such as those described in the Examples.

Identification of molecules that are able to bind to an Rspondin polypeptide may be accomplished by screening a compound, e.g. a peptide library with a recombinant soluble Rspondin polypeptide. To identify and isolate a compound that interacts and forms a complex with Rspondin, it is preferred to label or "tag" the Rspondin polypeptide. The Rspondin polypeptide may be conjugated to labelling groups, e.g. enzymes such as alkaline phosphatase or horseradish peroxidase or to other reagents such as fluorescent labels which may include fluorescein isothyiocynate (FITC), phycoerythrin (PE) or rhodamine. Conjugation of any given label to Rspondin may be performed using techniques that are routine in the art. polypeptide containing an epitope for which a commercially available antibody exists. The epitope-specific antibody may be tagged using methods well known in the art including labeling with enzymes, fluorescent dyes or colored or magnetic beads.

The "tagged" Rspondin polypeptide conjugate may be incubated with a library of immobilized compounds under suitable conditions, e.g. for 30 minutes to one hour at 22° C. to allow complex formation between the Rspondin polypeptide and an individual compound within the library. The library is then washed to remove any unbound Rspondin polypeptide. If Rspondin has been conjugated to alkaline phosphatase or horseradish peroxidase, the whole library may be poured into a petri dish containing a substrates for either alkaline phosphatase or peroxidase, for example, 5-bromo-4-chloro-3-indoyl phosphate (BCIP) or 3,3',4,4"-diamnobenzidine (DAB), respectively. After incubating for several minutes, the compound/solid phase-Rspondin complex changes color, and can be easily identified and isolated physically under a dissecting microscope with a micromanipulator. If a fluorescent tagged Rspondin molecule has been used, complexes may be isolated by fluorescent activated sorting. If a chimeric Rspondin polypeptide expressing a heterologous epitope has been used, detection of the compound/Rspondin complex may be accomplished by using a labeled epitope-specific antibody. Once isolated, the identity of the compound attached to the solid phase support may be determined, e.g. by peptide sequencing.

Cell lines or non-human transgenic animals that express Rspondin, e.g. Rspondin3, may be used to screen for regulators or effectors or modulators of Rspondin in a number of ways.

The ability of a regulator or effector or modulator of Rspondin to interfere with Rspondin activity and/or Rspondin signal transduction may be measured using an endothelial proliferation assay, a chicken CAM assay or a *Xenopus* VMZ differentiation assay. Other responses such as activation or suppression of catalytic activity, phosphorylation or dephosphorylation of other proteins, activation or modulation of second messenger production, changes in cellular ion levels, association, dissociation or translocation of signalling molecules, or transcription or translation of specific genes may also be monitored. These assays may be performed using conventional techniques developed for these purposes in the course of screening.

Ligand binding to its cellular receptor may, via signal transduction pathways, affect a variety of cellular processes. Cellular processes under the control of the Rspondin signaling pathway may include, but are not limited to, normal cellular functions, proliferation, differentiation, maintenance of cell shape, and adhesion, in addition to abnormal or potentially deleterious processes such as unregulated cell proliferation, loss of contact inhibition, blocking of differentiation or cell death. The qualitative or quantitative observation and measurement of any of the described cellular processes by techniques known in the art may be advantageously used as a means of scoring for signal transduction in the course of screening.

Various embodiments are described below for screening, identification and evaluation of compounds that interact with Rspondin, which compounds may affect various cellular processes under the control of the Rspondin signalling pathway.

The present invention includes a method for identifying a regulator, effector or modulator of Rspondin, comprising:

(a) contacting the putative regulator, effector or modulator of Rspondin with an Rspondin polypeptide, in pure or semi-pure form, or in a whole live or fixed cell or in a non-human transgenic animal, (b) measuring the effect of the putative regulator, effector or modulator of Rspondin on the Rspondin polypeptide, the activity of the Rspondin, and/or on a phenotypic property of the cell or the organism mediated by the Rspondin, (c) comparing the measured effect to that without the putative regulator, effector or modulator of Rspondin, thereby determining whether the putative regulator, effector or modulator of Rspondin stimulates or inhibits the intracellular response of the Rspondin.

Rspondins, e.g. Rspo3, useful in identifying a regulator, effector or modulator of Rspondin may be functionally equivalent to Rspondin. A functional equivalent to Rspondin may be prepared from a naturally occurring or recombinantly expressed Rspondin by proteolytic cleavage followed by conventional purification procedures known to those skilled in the art. Alternatively, the functional derivative may be produced by recombinant DNA technology by expressing parts of Rspondin which include the functional domain in suitable cells. Functional derivatives may also be chemically synthesized. Cells expressing Rspo3 may be used as a source of Rspondin, crude or purified, for testing in these assays. Alternatively, whole live or fixed cells may be used directly in those assays.

Rspondin signal transduction activity may be measured by an endothelial proliferation assay, a chicken CAM assay or a *Xenopus* VMZ differentiation assay and/or by monitoring the cellular processes controlled by the signal.

The invention also includes a method whereby a molecule capable of binding to an Rspondin polypeptide may be identified comprising:

(a) immobilizing an Rspondin polypeptide or a functional equivalent thereof to a solid phase matrix;

(b) contacting the molecule with the solid phase matrix produced in step (a), for an interval sufficient to allow the molecule to bind;

(c) washing away any unbound material from the solid phase matrix;

(d) detecting the presence of the molecule bound to the solid phase.

The above method may further include the step of:

(e) eluting the bound molecule from the solid phase matrix, thereby isolating the molecule.

The above method may further include the step of:

(f) identifying the molecule eluted.

Various procedures known in the art may be used for the production of antibodies to epitopes of an Rspondin polypeptide, e.g. Rpo2 or Rspo3.

Monoclonal antibodies that bind to an Rspondin polypeptide may be radioactively labelled allowing one to follow their location and distribution in the body after injection. Radioactivity tagged antibodies may be used as a non-invasive diagnostic tool for imaging de novo vascularization associated with conditions where treatment involves inhibiting angiogenesis and/or vasculogenesis.

Immunotoxins may also be designed which target cytotoxic agents to specific sites in the body. For example, high affinity Rspondin-specific monoclonal antibodies may be covalently complexed to bacterial or plant toxins, such as diptheria toxin, abrin or ricin. A general method of preparation of antibody/hybrid molecules may involve use of thiol-crosslinking reagents such as SPDP, which attack the primary amino groups on the antibody and by disulfide exchange, attach the toxin to the antibody. The hybrid antibodies may be used to specifically eliminate Rspondin expressing endothelial cells.

For the production of antibodies, various host animals may be immunized by injection with the Rspondin polypeptide including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Monoclonal antibodies to Rspondin may be prepared by using any technique which provides for the production of antibody molecules by continuous cell lines in culture. These include but are not limited to the hybridoma technique originally described by Kohler and Milstein, (Nature, 1975, 256: 495-497), the human B-cell hybridoma technique (Kosbor et al., 1983, Immunology Today, 4: 72; Cote et al., 1983, Proc. Natl. Acad. Sci., 80: 2026-2030) and the EPV-hybridoma technique (Cole et al., 1985, Monoclonal Antibodies and Cancer Therapy, Alan R. Liss, Inc., pp. 77-96). In addition, techniques developed for the production of "chimeric antibodies" (Morrison et al., 1984, Proc. Natl. Acad. Sci., 81: 6851-6855; Neuberger et al., 1984, Nature, 312: 604-608; Takeda et al., 1985, Nature, 314: 452-454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946, 778) can be adapted to produce Rspondin-specific single chain antibodies.

Antibody fragments which contain specific binding sites for Rspo3 may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246: 1275-1281) to allow rapid and easy identification of monoclonal Fab fragments with the desired specificity to Rspondin.

Antibodies to Rspondin polypeptides may antagonise the activity of Rspondin by preventing it from binding to its usual partner in the Wnt signalling cascade. Therefore, antibodies which bind specifically to Rspondin, in particular to Rspo2 or Rspo3, may be antagonists of Rspondin which may be used to inhibit angiogenesis and/or vasculogenesis.

In addition, mutated forms of Rspondin, having a dominant negative effect, may be expressed in targeted cell populations to inhibit the activity of endogenously expressed wild-type Rspo3.

Included in the scope of the invention are nucleic acid antagonists of Rspondin. Anti-sense RNA and DNA molecules act to directly block the translation of mRNA by binding to targeted mRNA and preventing protein translation. In regard to antisense DNA, oligodeoxyribonucleotides derived from the translation initiation site, e.g., between −10 and +10 regions of the Rspondin nucleotide sequence, are preferred.

Ribozymes are enzymatic RNA molecules capable of catalyzing the specific cleavage of RNA. The mechanism of ribozyme action involves sequence-specific hybridization of the ribozyme molecule to complementary target RNA, followed by a endonucleolytic cleavage. Within the scope of the invention are engineered hammerhead motif ribozyme molecules that specifically and efficiently catalyze endonucleolytic cleavage of Rspo3 RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

RNAi molecules are double-stranded RNA molecules or analogues thereof capable of mediating RNA interference of a target mRNA molecule, e.g. siRNA molecules which are short double-stranded RNA molecules with a length of preferably 19-25 nucleotides and optionally at least one 3'-overhang or precursors thereof or DNA molecules coding therefor. Anti-sense RNA and DNA molecules, ribozymes and RNAi molecules of the invention may be prepared by any method known in the art for the synthesis of RNA molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include but are not limited to the addition of flanking sequences of Morpholino derivatives as well as ribo- or deoxy-nucleotides to the 5' and/or 3' ends of the molecule or the use of phosphorothioate or 2' O-methyl rather than phosphodiesterase linkages within the oligodeoxyribonucleotide backbone.

Expression and functional activity of Rspo3 correlates with the development of the vasculature and endothelial cell proliferation, indicating that Rspo3 is involved in the vascularization process. Rspondins, such as Rspo2 or 3, induce VEGF, and VEGF has been shown to be a mitogenic growth factor known to act exclusively on endothelial cells (Ferrara, N. and Henzel, W. J., 1989, Biochem. Biophys. Res. Comm. 161: 851-858).

In one embodiment of the invention, Rspondin polypeptides such as Rspo2 or 3, can be administered in vivo to modulate angiogenesis and/or vasculogenesis. For example, the administration of Rspo2 or 3 may be used to treat conditions where treatment involves promoting angiogenesis and/or vasculogenesis, whereas antagonists of Rspo2 or 3 may be used to treat conditions where treatment involves inhibiting angiogenesis and/or vasculogenesis.

In a particular embodiment of the invention, Rspondin agonists may be used to treat conditions wherein treatment involves promoting angiogenesis and/or vasculogenesis. In a particular embodiment said conditions are selected from the group consisting of wound healing, tissue and organ regeneration or development, vasculodegenerative processes (e.g. critical limb- or brain ischemia, ischemic heart disease), embryonic development, and reproductive processes such as follicle development in the corpus luteum during ovulation and placental growth during pregnancy. In a further particular embodiment said condition is selected from wound healing, tissue and organ regeneration or development, vasculodegenerative processes (e.g. critical limb- or brain ischemia, ischemic heart disease).

In a particular embodiment of the invention the Rspondin agonist is an Rspo2 agonist or an Rspo3 agonist.

In a particular embodiment of the invention the Rspondin agonist is selected from an Rspondin polypeptide, an Rspondin nucleic acid or a small molecule. In a most particular embodiment of the invention an Rspondin polypeptide may be used to treat conditions wherein treatment involves promoting angiogenesis or vasculogenesis. In a most particular embodiment of the invention an Rspondin nucleic acid may be used to treat conditions wherein treatment involves promoting angiogenesis and/or vasculogenesis.

In a particular embodiment of the invention Rspondin antagonists may be used in the treatment of conditions where treatment involves inhibiting angiogenesis e.g. tumor growth and metastatic activity, atherosclerosis, stenosis, restenosis, retinopathy, macular degeneration, psoriasis and rheumatoid arthritis. In a particular embodiment said condition is solid tumor growth. In a further particular embodiment said condition is macular degeneration. In a further particular embodiment said condition is rheumatoid arthritis.

In a particular embodiment of the invention the Rspondin antagonist is an Rspo2 antagonist or an Rspo3 antagonist.

In a particular embodiment of the invention the Rspondin antagonist is selected from an Rspondin antibody or a nucleic acid capable of inhibiting Rspondin translation, transcription, expression and/or activity. In a most particular embodiment of the invention an Rspondin antibody may be used to treat conditions wherein treatment involves inhibiting angiogenesis or vasculogenesis. In a most particular embodiment of the invention a nucleic acid capable of inhibiting Rspondin translation, transcription, expression and/or activity may be used to treat conditions wherein treatment involves promoting angiogenesis or vasculogenesis. In a most particular embodiment of the invention an siRNA or antisense nucleic acid against Rspondin may be used to treat conditions where treatment involves promoting angiogenesis or vasculogenesis.

Pharmaceutically active regulators or effectors or modulators of Rspondin can be administered to a patient either by itself, or in pharmaceutical compositions where it is mixed with suitable carriers or excipient(s).

Depending on the specific conditions being treated, these agents may be formulated and administered systemically or locally. Techniques for formulation and administration may be found in "Remington's Pharmaceutical Sciences," Mack Publishing Co., Easton, Pa., latest edition. Suitable routes may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections, or, in the case of solid tumors, directly injected into a solid tumor. For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

The regulators or effectors or modulators of Rspondin can be formulated readily using pharmaceutically acceptable carriers well known in the art into dosages suitable for oral administration. Such carriers enable the regulators or effectors or modulators of Rspondin of the invention to be formulated as tablets, pills, capsules, liquids, gels, syrups, slurries, suspensions and the like, for oral ingestion by a patient to be treated.

Pharmaceutical compositions suitable for use in the present invention include compositions wherein the regulators or effectors or modulators of Rspondin are contained in an effective amount to achieve its intended purpose. Determination of the effective amounts is well within the capability of those skilled in the art, especially in light of the detailed disclosure provided herein.

In addition to the regulators or effectors or modulators of Rspondin these pharmaceutical compositions may contain suitable pharmaceutically acceptable carriers comprising excipients and auxiliaries which facilitate processing of the regulators or effectors or modulators of Rspondin into preparations which can be used pharmaceutically. The preparations formulated for oral administration may be in the form of tablets, dragees, capsules, or solutions.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical formulations for parenteral administration include aqueous solutions of the regulators or effectors or modulators of Rspondin in water-soluble form. Additionally, suspensions of the regulators or effectors or modulators of Rspondin may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the regulators or effectors or modulators of Rspondin to allow for the preparation of highly concentrated solutions.

Pharmaceutical preparations for oral use can be obtained by combining the regulators or effectors or modulators of Rspondin with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of regulators or effectors or modulators of Rspondin doses.

Pharmaceutical preparations which can be used orally include push-fit capsules made of gelatin, as well as soft, sealed capsules made of gelatin and a plasticizer, such as glycerol or sorbitol. The push-fit capsules can contain the regulators or effectors or modulators of Rspondin in admixture with filler such as lactose, binders such as starches, and/or lubricants such as talc or magnesium stearate and, optionally, stabilizers. In soft capsules, the regulators or effectors or modulators of Rspondin may be dissolved or suspended in suitable liquids, such as fatty oils, liquid paraffin, or liquid polyethylene glycols. In addition, stabilizers may be added.

Compositions comprising a regulators or effectors or modulators of Rspondin of the invention formulated in a compatible pharmaceutical carrier may be prepared, placed in an appropriate container, and labelled for treatment of an indicated condition. Suitable conditions indicated on the label may include treatment of a tumor, such as a glioma or glioblastoma; and. other conditions where treatment involves inhibiting angiogenesis and/or vasculogenesis.

Compositions comprising a regulators or effectors or modulators of Rspondin of the invention formulated in a compatible pharmaceutical carrier may be prepared, placed in an appropriate container, and labelled for treatment of an indicated condition. Suitable conditions indicated on the label may include treatment of a conditions where treatment involves promoting angiogenesis and/or vasculogenesis, in particular wound healing.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the regulators or effectors or modulators of Rspondin of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

For any regulator or effector or modulator of Rspondin used in the method of the invention, the therapeutically effective dose can be estimated initially from cell culture assays. For example, a dose can be formulated in animal models to achieve a circulating concentration range that includes the IC50 as determined in cell culture (i.e., the concentration of the test compound which achieves a half-maximal inhibition of the PTP activity). Such information can be used to more accurately determine useful doses in humans.

A therapeutically effective dose refers to that amount of the regulator or effector or modulator of Rspondin that results in amelioration of symptoms or a prolongation of survival in a patient. Toxicity and therapeutic efficacy of such regulators or effectors or modulators of Rspondin can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Regulators or effectors or modulators of Rspondin which exhibit large therapeutic indices are preferred. The data obtained from these cell culture assays and animal studies can be used in formulating a range of dosage for use in human. The dosage of such regulators or effectors or modulators of Rspondin lies preferably within a range of circulating concentrations that include the ED50 with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p 1).

Dosage amount and interval may be adjusted individually to provide plasma levels of the regulators or effectors or modulators of Rspondin which are sufficient to maintain the Rspo3 inhibitory or promoting effects. Usual patient dosages for systemic administration range from 1-2000 mg/day, commonly from 1-250 mg/day, and typically from 10-150 mg/day. Stated in terms of patient body weight, usual dosages range from 0.02-25 mg/kg/day, commonly from 0.02-3 mg/kg/day, typically from 0.2-1.5 mg/kg/day. Stated in terms of patient body surface areas, usual dosages range from 0.5-1200 mg/m$^2$/day, commonly from 0.5-150 mg/m$^2$/day, typically from 5-100 mg/m$^2$/day.

Dosage amount and interval may be adjusted individually to provide plasma levels of the regulator or effector or modulator of Rspondin which are sufficient to maintain the Rspondin inhibitory or promoting effects. Usual average plasma levels should be maintained within 50-5000 μg/ml, commonly 50-1000 μg/ml, and typically 100-500 μg/ml.

Alternately, one may administer the regulator or effector or modulator of Rspondin in a local rather than systemic manner, for example, via injection of the regulator or effector or modulator of Rspondin directly into a tumor, often in a depot or sustained release formulation.

Furthermore, one may administer the pharmaceutical composition in a targeted drug delivery system, for example, in a liposome coated with tumor-specific antibody. The liposomes will be targeted to and taken up selectively by the tumor.

In cases of local administration or selective uptake, the effective local concentration of the pharmaceutical composition may not be related to plasma concentration.

The Rspondin nucleic acids or compounds capable of binding to Rspondin, such as antibodies may be used for diagnostic purposes for detection of Rspondin expression in angiogenesis- and/or vasculogenesis-associated processes, conditions or disorders.

Reagents suitable for detecting Rspondins, such as Rspondin nucleic acids or compounds capable of binding to Respondin may have a number of uses for the diagnosis of processes, conditions or diseases resulting from, associated with and/or accompanied by, aberrant expression of Rspondin. The diagnostic procedures are preferably carried out on samples obtained from a subject, e.g. a human patient, e.g. samples from body fluids such as whole blood, plasma, serum or urine, or tissue samples such as biopsy or autopsy samples. For example, the Rspondin sequence may be used in amplification, e.g. hybridization assays to diagnose abnormalities of Rspondin expression; e.g., Southern or Northern analysis, including in situ hybridization assays.

The Rspondin cDNA may be used as a probe to detect the expression of the corresponding mRNA. In a specific example described herein, the expression of Rspo3 mRNA in mouse embryos was analyzed (FIG. 4). Rspo3 mRNA was found to be enriched in embryonic vessels, indicating a role for Rspo3 in endothelial cell proliferation.

Further, the present invention is explained in more detail by the following Example.

6 EXAMPLE

6.1 Materials and Methods

Rspo Coding Sequences

The nucleotide-coding sequence and deduced amino acid sequence of the murine and Xenopus Rspondin genes as deposited in Genbank used here are X. laevis Rspondin 2 [gi:54145367] (SEQ ID NO: 1)
X. tropicalis Rspondin 3 [gi:114149217] (SEQ ID NO: 2)
M. musculus Rspondin 3 [NM_028351] (SEQ ID NO: 3)

Mouse and Xenopus Embryos

Balb/c mice were mated overnight and the morning of vaginal plug detection was defined as ½ day of gestation. For routine histological analysis, tissues were fixed in 4% paraformaldehyde overnight and embedded in paraffin wax for sectioning. Generally, 4 µm sections were cut and stained with Hemalum and Eosine. For wholemount in situ hybridization, the embryos were fixed and processed as described (del Barco et al., 2003, Genes Dev. 17, 2239-2244). Xenopus embryos were obtained by in vitro fertilization and cultivated as described (Gawantka et al 1995 EMBO J. 14, 6268-79). Xenopus embryos were fixed and processed for whole mount in situ hybridization as described (Bradley et al., 1996 Development 122, 2739-2750). Ventral marginal zone were excised and cultivated as described (Gawantka et al 1995 EMBO J. 14, 6268-79). Full length Rspo3 cDNAs were used to generate antisense riboprobes.

Rspo3 knock out mice were obtained by targeted mutagenesis of murine Rspo3 (gi:94388197) in mouse embryonic stem cells following standard procedures, using a targeting vector shown in FIG. 5. Transgenic mice were generated on a C57BL/6 background via standard diploid injection. Homozygous mutant embryos were generated by heterozygote intercrosses. C57BL/6 heterozygotes were then backcrossed to CD1 females for at least 6 generations. No serious phenotypic differences were detected between homozygous embryos in C57BL/6 and CD1 background. Mouse tail tips or portions of yolk sacs or embryos were used for genotyping by PCR. Genotyping was routinely performed by PCR analysis using 3 primers, 5'-ATGCTTTGAGGCTTGT-GACC-3' (SEQ ID NO: 4), 5'-TGCACCGACTCCAG-TACTGG-3' (SEQ ID NO: 5) and 5'-TACATTCTG-GTTTCTCATCTGG-3' (SEQ ID NO: 6).

RT-PCR

RT-PCR assays were carried out as described (Gawantka et al 1995 EMBO J. 14, 6268-79); additional primers were; XSCL (forward, actcaccctccagacaagaa (SEQ ID NO: 7); reverse, atttaatcaccgctgcccac (SEQ ID NO: 8)); α-globin (forward, tccctcagaccaaaacctac (SEQ ID NO: 9); reverse, cccctcaattttatgctggac (SEQ ID NO: 10)); Xmsr (forward, aacttcgctctcgctcctccatac (SEQ ID NO: 11); reverse, gcca-gcagatagcaaacaccac (SEQ ID NO: 12)), VEGF (forward, aggcgagggagaccataaac (SEQ ID NO: 13); reverse, tctgctg-cattcacactgac (SEQ ID NO: 14)).

Preparation of Xenopus laevis Rspo2-Conditioned Medium

Transfection of HEK293T cells with Xenopus laevis Rspo2 (gi:54145367) and harvest of conditioned medium were as described (Kazanskaya et al., 2004, Dev. Cell 7, 525-534).

Endothelial Proliferation Assay

Human Umbilical Vein Endothelial Cells (HUVEC) (PromoCell) were cultured in Endothelial cell Growth Medium (Promocell) supplemented with 10% fetal bovine serum (FBS). For proliferation studies, cells were plated at 50% confluence in 96-well plate, next day they were supplemented with VEGF and Xenopus laevis Rspo2 proteins for 48 h, after which BrdU (10 µM) was added to each well for 4 h. BrdU analysis of cell proliferation was carried out using Cell Proliferation ELISA BrdU chemiluminescent from Roche Applied Science.

Chorioallantoic Membrane (CAM) Assay

For chicken chorioallantoic membrane (CAM) assay, chicken eggs were incubated at 37° C. in a humidified chamber. On day 3 of development, a window was made in the outer shell and on 6 day of development a 20 µl of Rspo2 or control beads or filter disk (3MM Whatman-8 mm diameter) carrying recombinant VEGF (Sigma-Aldrich, 100 ng/filter) was placed onto the surface of the CAM. The beads (ANTI-FLAG M2-Agarose, Sigma) were incubated overnight with Xenopus laevis Rspo2-conditioned medium or control medium from untransfected HEK 293T cells and washed 3 times in PBS. After 5 days of incubation, the filter disks and the attached CAM were excised, washed with PBS and processed for histology using Hematoxylin-Eosine staining.

Antisense Morpholino Oligonucleotide

Based on Xenopus tropicalis Rspo3 cDNA sequence (gi:114149217), an antisense morpholino oligonucleotide was designed (sequence: 5': atgcaattgcgactgctttctctgt (SEQ ID NO: 15)).

6.2 Results

FIG. 1 shows that an antisense morpholino oligonucleotide which is directed against Xenopus tropicalis Rspo3, inhibited the development of forming blood vessels in Xenopus tadpoles. A marker for forming blood vessels is the gene msr, which was down-regulated. Inhibition of blood vessel development—in other words embryonic angiogenesis—is accompanied by expansion of blood cell development, since blood cell markers α-globin and SCL are expanded. The results suggest that Rspo3 is a developmental regulator that switches cell fate between blood and blood vessel development. The specificity of the morpholino-induced phenotype for inhibition of Rspo3 is demonstrated by the rescue experiment in FIG. 2. In this experiment, the related molecule Rspo2 was able to revert the expansion of blood marker α-globin.

The ability of Rspo2 to promote angiogenesis in Xenopus embryos is shown in an ventral marginal zone (VMZ) assay FIG. 3. Overexpression of Rspo2 mRNA inhibits blood cell markers and induces the endothelial marker msr, as well as the angiogenic factor VEGF. Conversely, the requirement of endogenous Rspo3 for embryonic angiogenesis is shown by the inhibition of msr and VEGF by an antisense morpholino oligonucleotide.

By way of the examples in FIGS. 1-3 it is demonstrated that inhibition of Rspo3 in a vertebrate inhibits VEGF, vasculogenesis and angiogenesis. Therefore, antagonists of Rspo3 will be useful to deliberately inhibit VEGF, vasculogenesis and angiogenesis where this is useful, e.g. in conditions where treatment involves inhibiting angiogenesis and/or vasculogenesis.

The ability of Rspondins to promote angiogenesis is not limited to Xenopus but also extends to mammals, e.g. to the mouse. Rspo3 is expressed in murine embryonic blood vessels (FIG. 4). Furthermore, Rspo3 mutant mice show defective angiogenesis. This is demonstrated by the early lethality of such mutant mice, which show internal bleedings, as is characteristic for a failure to form blood vessels (FIG. 6). The deficient angiogenesis is also evidenced by the reduced blood vessels in the yolk sac of mutant embryos (FIG. 7). Furthermore, the inactivation of Rspo3 is accompanied with downregulation of VEGF in mutant placentas (FIG. 8). By way of these examples it is again demonstrated that inhibition of Rspo3 in a mammal inhibits VEGF, vasculogenesis and angiogenesis.

The ability of Rspo2 to induce angiogenesis is demonstrated in two standard in vitro angiogenesis assays. In the chicken choriallantois membrane (CAM) assay, the ability of regulators or effectors or modulators of Rspondin to promote the growth of endothelial cells and blood vessels is measured. A strong induction of endothelial cell growth and of blood vessels was observed following implantation of beads soaked with VEGF or Rspo2 conditioned medium (FIG. 9). Furthermore, Rspo2 conditioned medium induced branching morphogenesis in endothelial cells (FIG. 10), a characteristic response to angiogenic factors. In addition Rspo2 induced proliferation of endothelial cells, similar to the angiogenic factor VEGF (FIG. 11).

The present invention is not to be limited in scope by the exemplified embodiments which are intended as illustrations of single aspects of the invention, and any clones, DNA or functionally equivalents to Rspondin are within the scope of the invention. Indeed, various modifications of the invention in addition to those described herein will become apparent to those skilled in the art from the foregoing description and accompanying drawings. Such modifications are intended to fall within the scope of the appended claims.

All references cited herein are hereby incorporated by reference in their entirety.

The invention claimed is:

1. A method for inhibiting angiogenesis and/or vasculogenesis in a subject in need of such treatment comprising administering to the subject a therapeutically effective dose of an Rspondin2 antagonist, wherein the Rspondin2 antagonist is a nucleic acid molecule capable of inhibiting Rspondin2 translation, transcription, expression and/or activity.

2. The method of claim 1, wherein the Rspondin2 antagonist is an antisense molecule or siRNA molecule.

3. The method of claim 1, wherein the Rspondin2 antagonist is an antisense molecule capable of inhibiting transcription of Rspondin2 nucleic acid encoding Rspondin2 polypeptide comprising the amino acid sequence set out in SEQ ID NO:19 or an amino acid sequence having at least 90% identity to SEQ ID NO:19 or capable of inhibiting translation, expression and/or activity of Rspondin2 polypeptide comprising the amino acid sequence set out in SEQ ID NO:19 or an amino acid sequence having at least 90% identity to SEQ ID NO:19.

* * * * *